(12) United States Patent
Marshall et al.

(10) Patent No.: US 11,925,431 B2
(45) Date of Patent: *Mar. 12, 2024

(54) MOTION FEEDTHROUGH

(71) Applicant: CMR SURGICAL LIMITED, Cambridge (GB)

(72) Inventors: Keith Marshall, Cambridge (GB); Nikki Priyam Su-Ling Phoolchund, Cambridge (GB); Thomas Bates Jackson, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/956,202

(22) Filed: Sep. 29, 2022

(65) Prior Publication Data
US 2023/0022025 A1  Jan. 26, 2023

Related U.S. Application Data

(63) Continuation of application No. 16/321,757, filed on Jan. 29, 2019, now Pat. No. 11,564,763.

(30) Foreign Application Priority Data

Jul. 29, 2016  (GB) .................................... 1613093
Sep. 14, 2016  (GB) .................................... 1615615
(Continued)

(51) Int. Cl.
*A61B 46/17* (2016.01)
*A61B 17/00* (2006.01)
*A61B 34/30* (2016.01)

(52) U.S. Cl.
CPC .............. *A61B 46/17* (2016.02); *A61B 17/00* (2013.01); *A61B 34/30* (2016.02); *A61B 2017/00477* (2013.01); *A61B 2034/302* (2016.02)

(58) Field of Classification Search
CPC .......... A61B 46/17; A61B 34/30; A61B 17/00
See application file for complete search history.

(56) References Cited

U.S. PATENT DOCUMENTS

| 8,506,555 | B2 | 8/2013 | Ruiz Morales |
| 8,684,962 | B2 * | 4/2014 | Kirschenman ......... A61B 34/71 604/95.04 |

(Continued)

FOREIGN PATENT DOCUMENTS

| CN | 103702632 A | 4/2014 |
| CN | 104411266 A | 3/2015 |

(Continued)

OTHER PUBLICATIONS

English Translation of a Chinese First Notification of Office Action from corresponding Chinese Application No. 201780047136.X dated Jan. 13, 2021.
(Continued)

*Primary Examiner* — Nathaniel C Chukwurah
(74) *Attorney, Agent, or Firm* — Lando & Anastasi, LLP

(57) ABSTRACT

A motion feedthrough for a surgical drape, the motion feedthrough comprising a drive transfer element comprising a first portion and a second portion, the first portion being releasably engageable with a portion of a robot arm and the second portion being releasably engageable with a portion of an instrument, the drive transfer element being movable relative to a bulk portion of the drape so as to transfer drive between the robot arm and the instrument.

12 Claims, 11 Drawing Sheets

(30) Foreign Application Priority Data

Sep. 14, 2016 (GB) ...................................... 1615616
Sep. 19, 2016 (GB) ...................................... 1615919

(56) References Cited

U.S. PATENT DOCUMENTS

| | | |
|---|---|---|
| 9,568,992 B2 | 2/2017 | Hasegawa et al. |
| 10,335,243 B2 | 7/2019 | Yanagihara et al. |
| 10,603,126 B2 | 3/2020 | Karguth et al. |
| 11,654,763 B2 * | 5/2023 | Shih ..................... G06Q 10/083 701/41 |
| 2003/0151721 A1 | 8/2003 | Lai et al. |
| 2006/0052664 A1 * | 3/2006 | Julian ................ A61B 1/00128 600/152 |
| 2006/0161138 A1 | 7/2006 | Orban et al. |
| 2009/0248039 A1 | 10/2009 | Cooper et al. |
| 2010/0170519 A1 * | 7/2010 | Romo .................... A61B 34/30 606/130 |
| 2010/0175701 A1 | 7/2010 | Reis et al. |
| 2011/0168189 A1 | 7/2011 | Cooper et al. |
| 2011/0277775 A1 | 11/2011 | Holop et al. |
| 2012/0289973 A1 | 11/2012 | Prisco et al. |
| 2013/0317519 A1 | 11/2013 | Romo et al. |
| 2014/0001234 A1 | 1/2014 | Shelton, IV et al. |
| 2014/0001235 A1 * | 1/2014 | Shelton, IV ..... A61B 17/07207 227/176.1 |
| 2015/0148818 A1 | 5/2015 | Lohmeier et al. |
| 2015/0173726 A1 | 6/2015 | Lohmeier et al. |
| 2015/0173731 A1 | 6/2015 | Lohmeier et al. |
| 2015/0202009 A1 | 7/2015 | Nussbaumer et al. |
| 2015/0257841 A1 * | 9/2015 | Dachs, II ............... A61B 90/08 403/321 |
| 2016/0058513 A1 | 3/2016 | Giorgi et al. |
| 2016/0151120 A1 | 6/2016 | Kostrzewski et al. |

FOREIGN PATENT DOCUMENTS

| | | |
|---|---|---|
| CN | 104622583 A | 5/2015 |
| CN | 105163685 A | 12/2015 |
| CN | 105640647 A | 6/2016 |
| EP | 2886061 A2 | 6/2015 |
| GB | 2538230 A | 11/2016 |
| JP | 2009525098 A | 7/2009 |
| JP | 2012055377 A | 3/2012 |
| JP | 2013027733 A | 2/2013 |
| JP | 2013530738 A | 8/2013 |
| JP | 2015523147 A | 8/2015 |
| JP | 2016120277 A | 7/2016 |
| JP | 2019512319 A | 5/2019 |
| JP | 2019523071 A | 8/2019 |
| WO | 2007041093 A1 | 4/2007 |
| WO | 2009061915 A2 | 5/2009 |
| WO | 2010081050 A1 | 7/2010 |
| WO | 2011037394 A2 | 3/2011 |
| WO | 2014201538 A1 | 12/2014 |
| WO | 2015057821 A1 | 4/2015 |
| WO | 2015142793 A1 | 9/2015 |
| WO | 2016081286 A1 | 5/2016 |
| WO | 2016090459 A1 | 6/2016 |
| WO | 2016097861 A1 | 6/2016 |
| WO | 2016178028 A1 | 11/2016 |
| WO | 2017015167 A1 | 1/2017 |
| WO | 2017158263 A1 | 9/2017 |
| WO | 2018020252 A2 | 2/2018 |
| WO | 2018020254 A2 | 2/2018 |

OTHER PUBLICATIONS

English Translation of a Japanese Notification of Reason for Refusal from corresponding Japanese Patent Application No. 2019-504801 dated May 13, 2021.
English Translation of a Japanese Notification of Reasons for Refusal from corresponding Japanese Application No. 2019-504781 dated May 11, 2021.
Indian Examination Report from corresponding Indian Application No. 201917007380 dated Apr. 30, 2021.
International Search Report and Written Opinion from corresponding PCT/GB2017/052192 dated Oct. 30, 2017.
Japanese Decision to Grant a Patent from corresponding Japanase Patent Application No. 2019504801 dated Jun. 23, 2022.
Japanese Notification of Reasons for Refusal from corresponding Japanese Patent Application No. 2019-054794 dated Jun. 15, 2021 [English translation attached].
Notification of Transmittal of the International Search Report and the Written Opinion of the International Searching Authority from corresponding PCT/GB2017/052193 dated Jan. 30, 2018.
Notification of Transmittal of the International Search Report and the Written Opinion of the International Searching Authority from corresponding PCT/GB2017/052195 dated Jan. 30, 2018.
United Kingdom Combined Search and Examination Report from corresponding United Kingdom Application No. GB2114611.3 dated Nov. 19, 2021.
United Kingdom Examination Report from corresponding United Kingdom Application No. GB1613093.2 dated Mar. 22, 2021.
United Kingdom Search Report from corresponding United Kingdom Application No. GB1613093.2 dated Jan. 27, 2017.
United Kingdom Search Report from corresponding United Kingdom Application No. GB1615615.0 dated Feb. 16, 2017.
United Kingdom Search Report from corresponding United Kingdom Application No. GB1615616.8 dated Feb. 22, 2017.
United Kingdom Search Report from corresponding United Kingdom Application No. GB1615918.8 dated Feb. 16, 2017.
United Kingdom Search Report from corresponding United Kingdom Application No. GB1615919.6 dated Feb. 23, 2017.
Japanese Notification of Reasons for Refusal from corresponding Japanese Application No. 2021-214509 dated Dec. 13, 2022.
Japanese Notification of Reasons for Refusal from corresponding Japanese Application No. 2022-012276 dated Dec. 6, 2022.

* cited by examiner

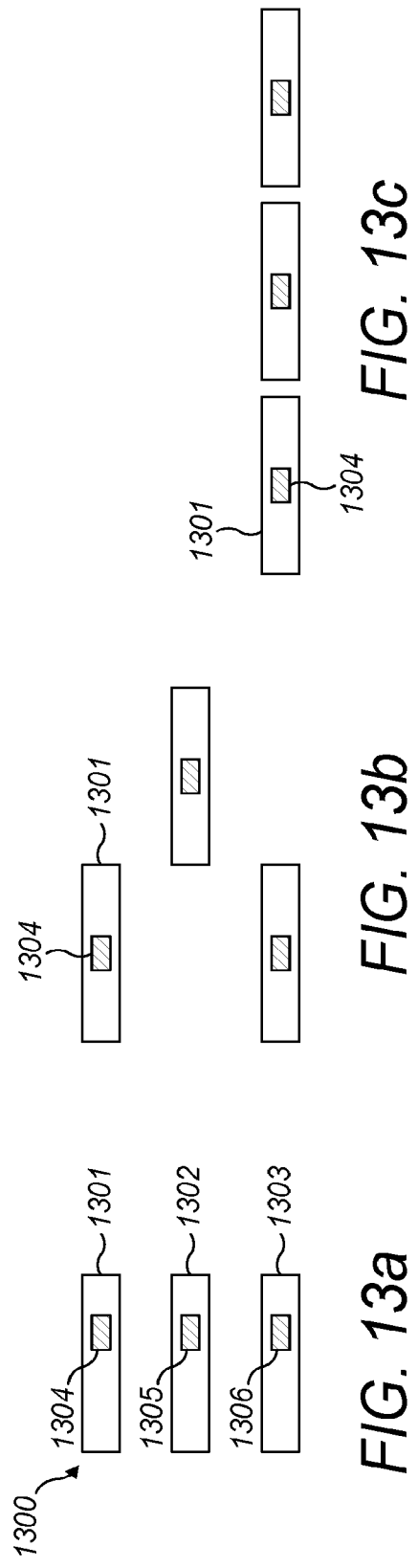

MOTION FEEDTHROUGH

CROSS-REFERENCE TO RELATED APPLICATIONS

This application is a continuation of U.S. patent application Ser. No. 16/321,757 [now U.S. Pat. No. 11,564,763], filed Jan. 29, 2019, which is a U.S. National Phase Application under 35 U.S.C. § 371 of International Application No. PCT/GB2017/052195 [Expired], filed Jul. 27, 2017, which claims priority to United Kingdom Application Nos. 1613093.2, filed Jul. 29, 2016, 1615615.0, filed Sep. 14, 2016, 1615616.8, filed Sep. 14, 2016, and 1615919.6, filed Sep. 19, 2016. Each application referenced above is hereby incorporated by reference in its entirety for all purposes.

BACKGROUND

It is known to use robots for assisting and performing surgery. FIG. 1 illustrates a surgical robot 100 which consists of a base 108, an arm 102, and an instrument 105 comprising an end effector 106. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient 101. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

The robotic arm 102 is shrouded by a surgical drape 109 to provide a sterile boundary between the surgical instrument (which must be sterile) and the robotic arm (which may not be sterile). The drape provides a boundary between the robotic arm and the sterile field in which the arm is positioned (for example an operating theatre).

FIG. 2 illustrates a surgical instrument 200 for performing robotic laparoscopic surgery. The surgical instrument comprises an instrument base 201 by means of which the surgical instrument connects to the robot arm. A shaft 202 extends between the instrument base 201 and an articulation 203. The articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation. The articulation 203 may be mechanically driven by a drive assembly powered by one or more motors housed within the robot arm. Mechanical drive needs to be connected, or coupled, to the instrument through the surgical drape.

A surgeon utilises many instruments during the course of a typical laparoscopy operation. For this reason, it is desirable for the instruments to be detachable from and attachable to the end of the robot arm with an ease and speed which enables instruments to be exchanged mid-operation. It is therefore desirable to minimise the time taken and maximise the ease with which one instrument is detached from a robot arm and a different instrument is attached.

The connection of the mechanical drive through the surgical drape presents difficulties when attempting to maintain the sterile barrier provided by the drape.

There is a need for an improved type of motion feedthrough.

SUMMARY

According to an aspect of the present invention, there is provided a motion feedthrough for a surgical drape, the motion feedthrough comprising:
a drive transfer element comprising a first portion and a second portion, the first portion being releasably engageable with a portion of a robot arm and the second portion being releasably engageable with a portion of an instrument, the drive transfer element being movable relative to a bulk portion of the drape so as to transfer drive between the robot arm and the instrument.

Suitably the motion feedthrough is operable to transfer drive without compromising the integrity of the surgical drape. Suitably the motion feedthrough is configured to substantially close a hole in the drape and/or be attachable to the periphery of a hole in the drape so as to maintain a substantially hermetic sterile barrier.

Suitably the motion feedthrough comprises a first longitudinally extending element and a second longitudinally extending element, the first and second longitudinally extending elements being slidingly engageable with one another along at least a portion of their length. Suitably the first longitudinally extending element comprises a tongue and the second longitudinally extending element comprises a groove, the tongue being engagingly receivable within the groove.

Suitably at least one of the first and the second longitudinally extending elements comprises a recess for receiving a plug.

Suitably at least one of the first longitudinally extending element and the second longitudinally extending element is attachable to the periphery of a hole in the drape, so that at least a portion of the drape will move together with the respective longitudinally extending element.

Suitably the motion feedthrough comprises a pair of capture members defining therebetween a capture portion for slidably capturing a portion of the drape. Suitably the motion feedthrough comprises three capture members defining between a first capture member and a second capture member a first capture portion, and defining between the second capture member and a third capture member a second capture portion, the first capture portion and the second capture portion being for slidably capturing a portion of the drape.

Suitably the capture members comprise one or more of a low-friction material and rollers.

Suitably the motion feedthrough comprises a rod configured to extend to both sides of the drape, the rod comprising an engaging portion towards each end of the rod. Suitably the motion feedthrough comprises a tube surrounding at least a portion of the rod, such that the rod extends beyond the tube, the tube comprising an engaging portion towards each end of the tube.

Suitably at least one of the rod and the tube is movable in a direction which is one or more of along its length and about its circumference.

Suitably the motion feedthrough comprises at least one of a clamp and an O-ring engageable with the drape.

Suitably the motion feedthrough comprises a hub engageable with the drape, the hub being rotatably movable relative to at least one of the robot arm and the instrument. Suitably the hub is engageable with the drape. Suitably the motion feedthrough comprises an interface structure engageable with the drape, the interface structure comprising a recess, and the hub being receivably engageable with the recess.

Suitably the hub comprises the first portion and the second portion, each of the first portion and the second portion being one of a pin and at least a portion of a cog wheel.

Suitably the motion feedthrough comprises a plurality of drive transfer elements, the drive transfer elements being linearly movable. Suitably the plurality of drive transfer elements are movable parallel to one another.

Suitably paths defined by movement of each drive transfer element are non-overlapping in a direction transverse to a direction of movement of at least one drive transfer element.

Suitably paths defined by movement of each drive transfer element at least partially overlap in a direction transverse to a direction of movement of at least one drive transfer element.

Suitably paths defined by movement of each drive transfer element are aligned along a common line. Suitably paths defined by movement of each drive transfer element are in a common plane.

Any one or more feature of any aspect above may be combined with any one or more feature of that aspect and/or any other aspect above. Any apparatus feature may be written as a method feature where possible, and vice versa. These have not been written out in full here merely for the sake of brevity.

This Summary is provided to introduce a selection of concepts in a simplified form that are further described below in the Detailed Description. The mention of features in this Summary does not indicate that they are key features or essential features of the invention or of the claimed subject matter, nor is it to be taken as limiting the scope of the claimed subject matter.

BRIEF DESCRIPTION OF THE FIGURES

The present invention will now be described by way of example with reference to the accompanying drawings. In the drawings:

FIG. 11b illustrates the other side of the interface structure of FIG. 11a;

FIG. 12b schematically illustrates a plan view of the alternative interface structure shown in FIG. 12a; and FIGS. 13a to 13c illustrate configurations of drive assembly interface elements.

DETAILED DESCRIPTION

Figure 3:
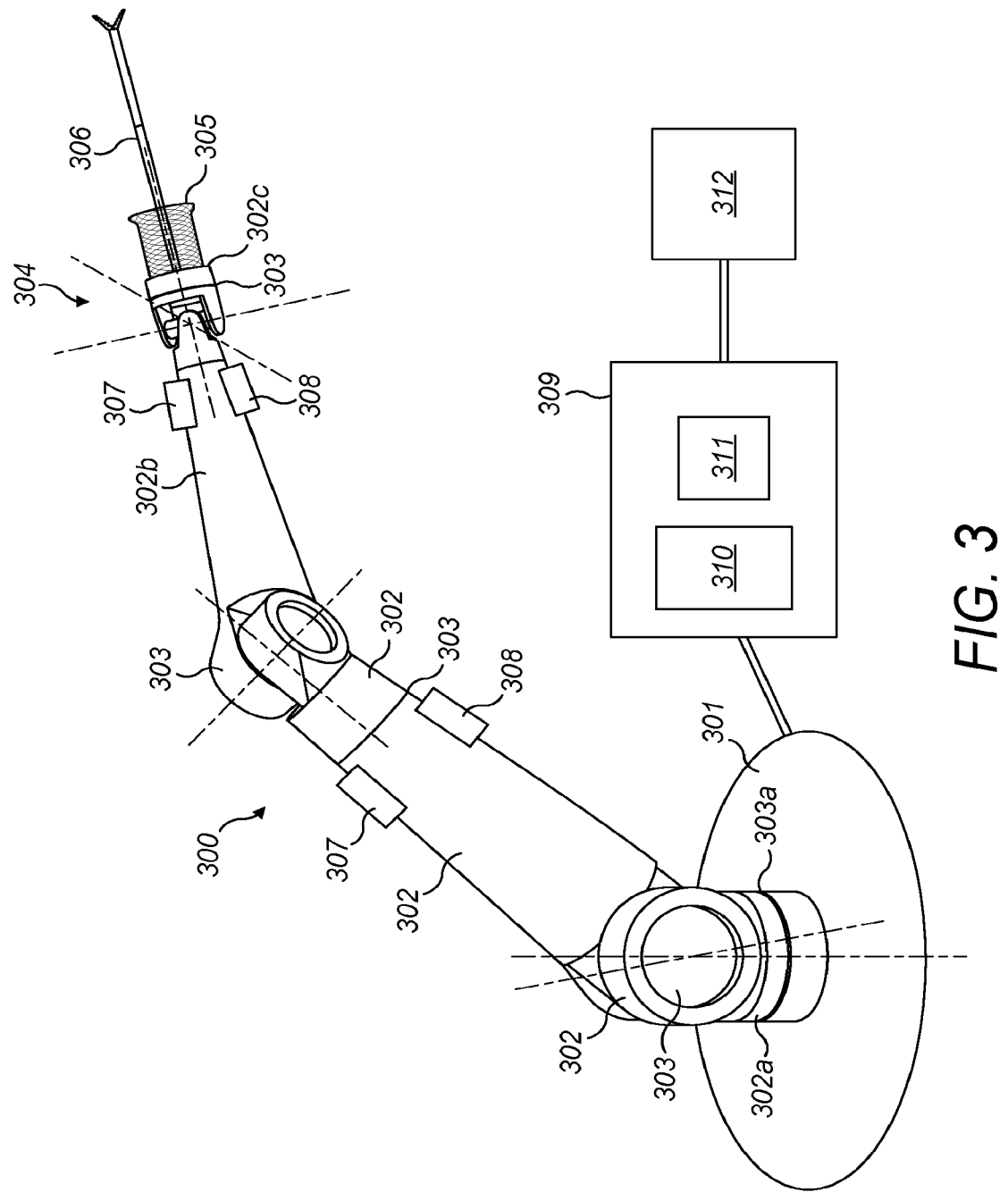
FIG. 3 illustrates a surgical robot.

FIG. 3 illustrates a surgical robot having an arm 300 which extends from a base 301. The arm comprises a number of rigid limbs 302. The limbs are coupled by revolute joints 303. The most proximal limb 302a is coupled to the base by a proximal joint 303a. It and the other limbs are coupled in series by further ones of the joints 303. Suitably, a wrist 304 is made up of four individual revolute joints. The wrist 304 couples one limb (302b) to the most distal limb (302c) of the arm. The most distal limb 302c carries an attachment 305 for a surgical instrument 306. Each joint 303 of the arm has one or more motors 307 which can be operated to cause rotational motion at the respective joint, and one or more position and/or torque sensors 308 which provide information regarding the current configuration and/or load at that joint. Suitably, the motors are arranged proximally of the joints whose motion they drive, so as to improve weight distribution. For clarity, only some of the motors and sensors are shown in FIG. 3. The arm may be generally as described in our co-pending patent application PCT/GB2014/053523.

Figure 1:
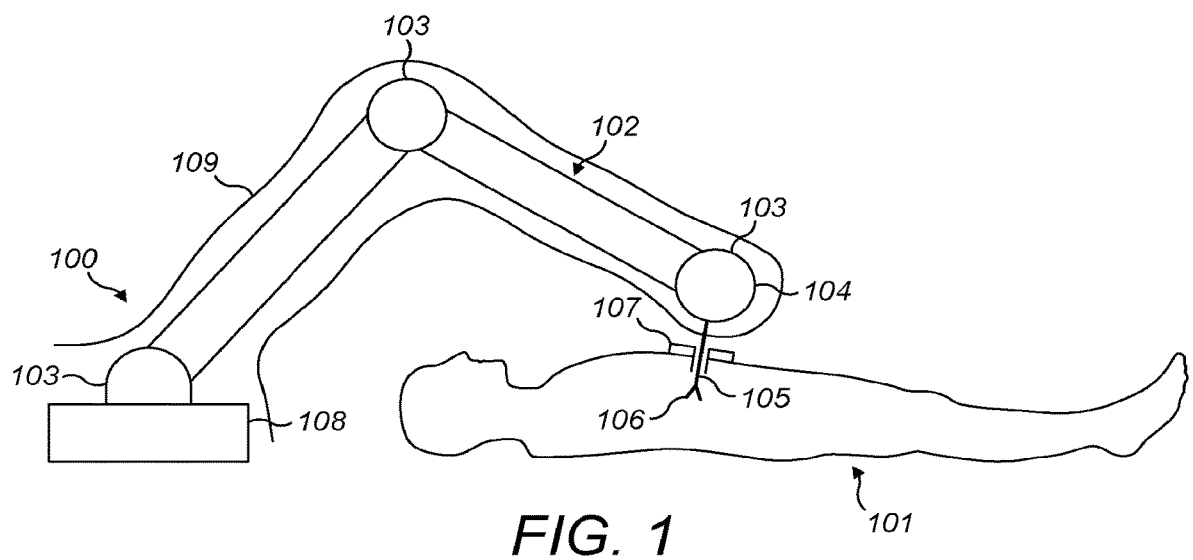
FIG. 1 illustrates a surgical robot performing a surgical procedure.
Figure 2:
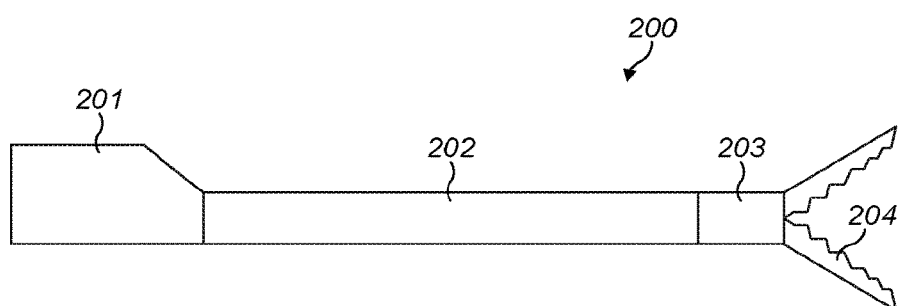
FIG. 2 illustrates a known surgical instrument.

The arm terminates in the attachment 305 for interfacing with the instrument 306. Suitably, the instrument 306 takes the form described with respect to FIG. 2. The instrument has a diameter less than 8 mm. Suitably, the instrument has a 5 mm diameter. The instrument may have a diameter which is less than 5 mm. The instrument diameter may be the diameter of the shaft. The instrument diameter may be the diameter of the profile of the articulation. Suitably, the diameter of the profile of the articulation matches or is narrower than the diameter of the shaft. The attachment 305 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable to and detachable from the robot arm during the operation. Features of the drive assembly interface and the instrument interface aid their alignment when brought into engagement with each other, so as to reduce the accuracy with which they need to be aligned by the user.

The instrument 306 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation comprises several joints which permit the end effector to move relative to the shaft of the instrument. The joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed within the robot arm. The controllers are connected via a communication bus to a control unit 309. The control unit 309 comprises a processor 310 and a memory 311. The memory 311 stores in a non-transient way software that is executable by the processor to control the operation of the motors 307 to cause the arm 300 to operate in the manner described herein. In particular, the software can control the processor 310 to cause the motors (for example via distributed controllers) to drive in dependence on inputs from the sensors 308 and from a surgeon command interface 312. The control unit 309 is coupled to the motors 307 for driving them in accordance with outputs generated by execution of the software. The control unit 309 is coupled to the sensors 308 for receiving sensed input from the sensors, and to the command interface 312 for receiving input from it. The respective couplings may, for example, each be electrical or optical cables, or may be provided by a wireless connection. The command interface 312 comprises one or more input devices whereby a user can request motion of the end effector in a desired way. The input devices could, for example, be manually operable mechanical input devices such as control handles or joysticks, or contactless input devices such as optical gesture sensors. The software stored in the memory 311 is configured to respond to those inputs and cause the joints of the arm and instrument to move accordingly, in compliance with a predetermined control strategy. The control strategy may include safety features which moderate the motion of the arm and instrument in response to command inputs. Thus, in summary, a surgeon at the command interface 312 can control the instrument 306 to move in such a way as to perform a desired surgical procedure. The control unit 309 and/or the command interface 312 may be remote from the arm 300.

Figure 4:
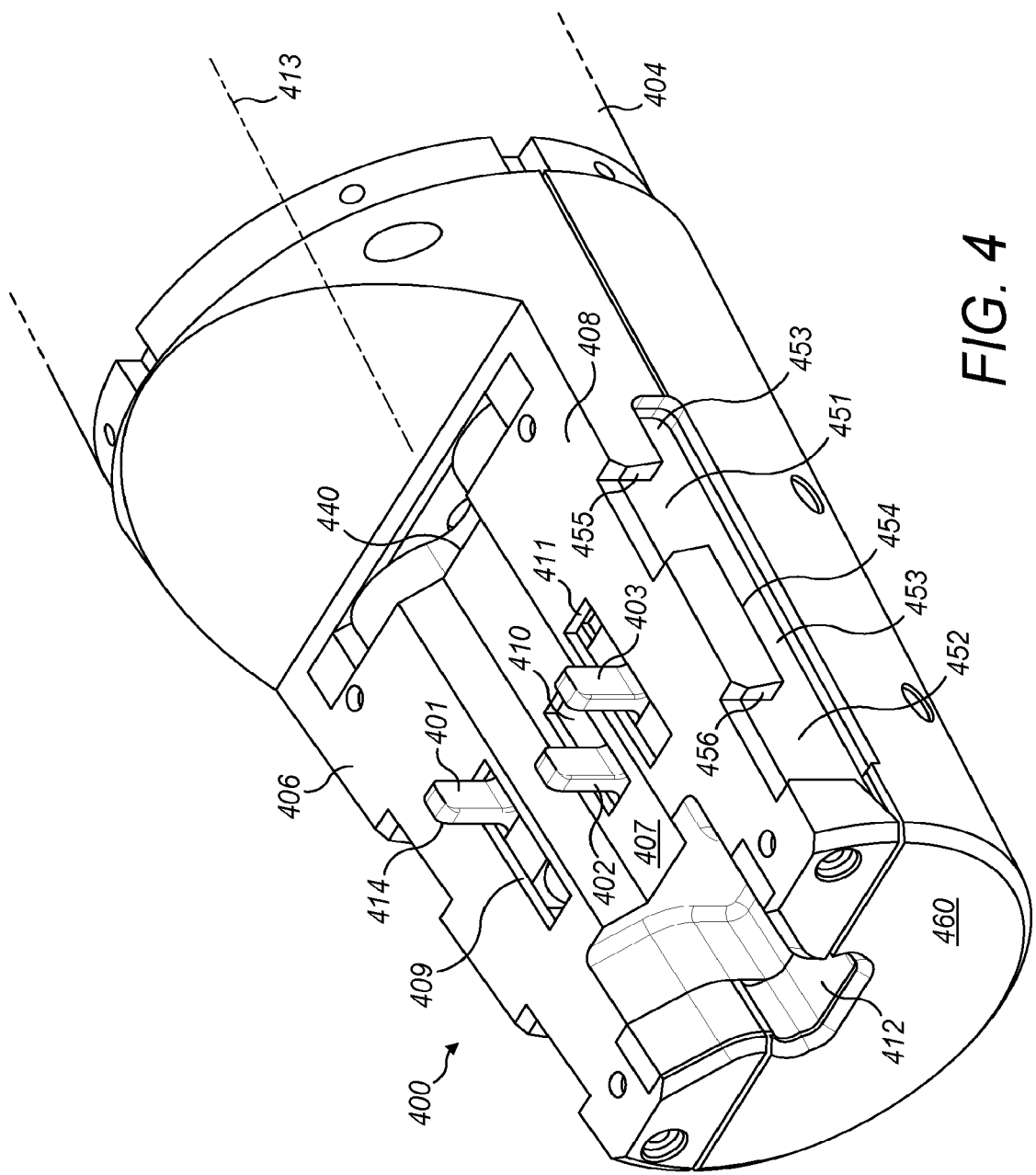
FIG. 4 illustrates a drive assembly interface of a surgical robot arm.
Figure 5:
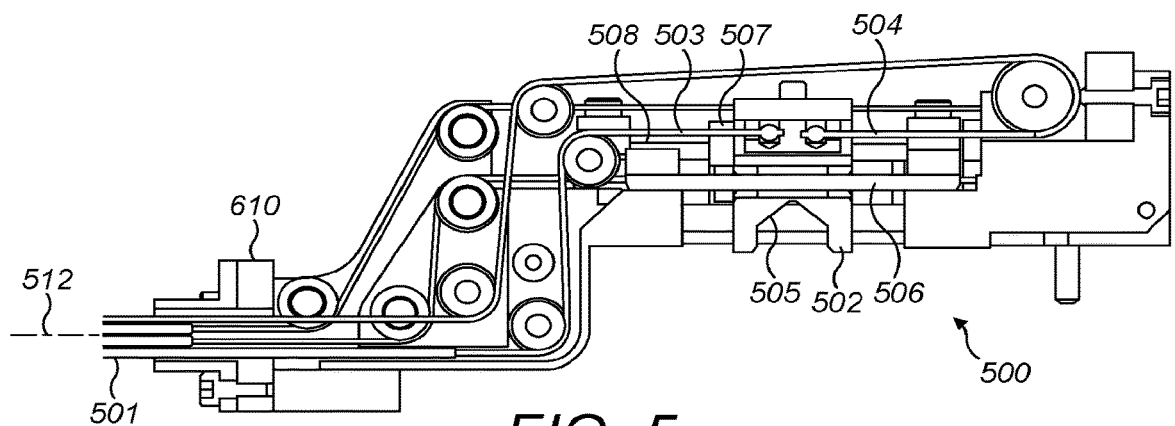
FIG. 5 illustrates an instrument interface of a surgical instrument.

FIGS. 4 and 5 illustrate an exemplary mechanical interconnection of the drive assembly interface and the instrument interface in order to transfer drive from the robot arm to the instrument. FIG. 4 illustrates an exemplary drive assembly interface 400 at the end of a robot arm 404. The drive assembly interface 400 comprises a plurality of drive assembly interface elements 401, 402, 403. The drive assembly interface elements protrude from surfaces 406, 407, 408 on the drive assembly interface 400. The protrusion of the drive assembly interface elements from the drive assembly interface 400 permits engagement of the drive assembly interface elements with corresponding instrument interface elements, as described below. The protrusions are in the form of fins in the illustrated example. In other implementations, other types of protrusion can be provided. The drive assembly interface elements suitably comprise a stiff material, such as a metal. Suitably the protrusion is formed from a stiff material, such as a metal. Preferably the drive assembly interface element is formed from a stiff material, such as a metal.

The protrusions (the fins in the illustrated example) comprise a chamfer 414 at their distal ends. The chamfer provides for ease of engagement of the protrusions in corresponding recesses, as described below. In other examples the distal ends of the protrusions can be provided with a rounded corner. The edges of the chamfered portions can be rounded.

The fins extend through the surfaces 406, 407, 408. The portions of the fins that protrude from the surfaces are perpendicular to the plane of the surfaces. In other examples the fins can protrude in a direction that is within a range of 10 degrees from perpendicular. Preferably the direction in which the fins extend is within a range of 5 degrees or within a range of 2 degrees from perpendicular.

FIG. 4 illustrates three drive assembly interface elements. In other examples, there may be greater than or fewer than three drive assembly interface elements. The drive assembly interface elements 401, 402, 403 are movable within the drive assembly interface 400 along linear paths 409, 410, 411. The paths can be parallel with one another. Suitably at least two of the paths are parallel. The paths need not be precisely parallel with one another. There may be some tolerance in how closely aligned the paths need to be. For example, the paths may be within 10 degrees of each other. The paths may extend in respective directions within a 10 degree range. Preferably the paths are within 5 degrees of each other, or within 2 degrees or 1 degree of each other. The paths may extend in respective directions within a 5 degree range, or preferably a 2 degree or 1 degree range.

Aligning the paths in this manner can assist in providing corresponding mechanisms more compactly. For instance, the mechanisms can be arranged to move alongside one another, permitting the mechanisms to be arranged more closely together. It is desirable for the robotic system to be highly dextrous. A small and/or light configuration can assist in providing a highly dextrous system. Arranging the mechanisms of the interfaces, and/or drive transfer elements, to be more compact (in either or both of a length, a width and a depth) can permit a smaller and/or lighter configuration.

In the illustrated example, the linear paths 409, 410, 411 are disposed on two parallel planes. The central linear path 410 is disposed on a plane 407 set into the drive assembly interface 400 compared to that in which the outer two linear paths 409, 411 are disposed. This arrangement permits a more compact interface between the drive assembly interface 400 and an instrument interface 500.

In other implementations, the three linear paths 409, 410, 411 can be disposed on the same plane, or all on different planes. In another example, the outer two linear paths 409, 411 are disposed on a plane set into the drive assembly interface 400 compared to that in which the central linear path 410 is disposed. In implementations utilising differing numbers of drive assembly interface elements, different configurations of planes on which the paths are disposed are possible.

Referring now to FIG. 5, the shaft 501 of the instrument terminates in the instrument interface 500. The instrument interface 500 comprises a plurality of instrument interface elements (one of which is shown at 502 in FIG. 5). The instrument interface elements suitably comprise a stiff material, such as a metal. Suitably the instrument interface element is formed from a stiff material, such as a metal. Pairs of driving elements (one such pair is shown at 503, 504) extend into the instrument interface 500 from the end of the shaft 501. Each pair of driving elements terminates in one of the instrument interface elements. In the example shown in FIG. 5, the driving element pair 503, 504 terminates in instrument interface element 502; likewise, other driving element pairs terminate in corresponding instrument interface elements.

In the illustrated example there are three driving element pairs that terminate in three instrument interface elements. In other examples, there may be greater than or fewer than three instrument interface elements. There may be greater than or fewer than three driving element pairs. In FIG. 5 there is a one-to-one relationship between instrument interface elements and driving element pairs. In other examples, there may be any other coupling relationship between the instrument interface elements and driving element pairs. For example, a single instrument interface element may drive more than one pair of driving elements. In another example, more than one instrument interface element may drive a single pair of driving elements.

Each instrument interface element 502 comprises a recess, or cup 505, which is the portion of the instrument interface element engageable with the drive assembly interface element.

The instrument interface elements are displaceable within the instrument interface. In the example shown, the instrument interface elements are slideable along rails. Instrument interface element 502 is slideable along rail 506. Each instrument interface element is displaceable along a direction parallel to the direction of elongation of the pair of driving elements which that instrument interface element holds captive. Each instrument interface element is displaceable in a direction parallel to the longitudinal axis 512 of the instrument shaft 501. When the instrument interface element moves along its respective rail, it causes a corresponding movement to the driving element pair secured to it. Thus, moving an instrument interface element drives motion of a driving element pair and hence motion of a joint of the instrument.

Drive assembly interface 400 mates with instrument interface 500. The instrument interface 500 comprises structure for receiving the drive assembly interface elements 401, 402, 403. Specifically, the instrument interface elements receive the drive assembly interface elements. In the example shown, each instrument interface element comprises a socket or cup 505 for receiving the fin of the corresponding drive assembly interface element. The socket 505 of one instrument interface element 502 receives a fin of the corresponding drive assembly interface element 402. Similarly, sockets of the other instrument interface elements receive fins of the other drive assembly interface elements.

Each drive assembly interface element is displaceable within the drive assembly. This displacement is driven. For example, the displacement may be driven by a motor and lead screw arrangement.

Each drive assembly interface element is displaceable along a direction parallel to the longitudinal axis 413 of the terminal link of the robot arm. When the drive assembly interface element moves, it causes a corresponding movement to the instrument interface element to which it is engaged. Thus, driving motion of a drive assembly interface element drives motion of an instrument interface element which drives articulation of the end effector of the instrument.

The portions of the fins that protrude from the surfaces comprise front and rear faces aligned in the directions of movement of the drive assembly interface elements. Here, front and rear refer to movement in one direction, when the front face will face the direction of movement and the rear face will face away from the direction of movement. When the drive assembly interface element moves in the opposite direction, the front face will face away from the direction of movement and the rear face will face the direction of movement.

The front and rear faces of the drive assembly interface elements are transverse to the direction in which the drive assembly interface elements are driveably movable. The front and rear faces of the drive assembly interface elements are parallel to the direction in which the fins protrude from the surfaces. The front and rear faces need not be exactly parallel to this direction, but are preferably within a range of 10 degrees, or within a range of 5 degrees, or more preferably within a range of 2 degrees of this direction.

The socket 505 comprises an interior face that is transverse to the direction in which the instrument interface elements are movable. The interior face need not be exactly transverse to this direction, but is preferably within a range of 10 degrees, or within a range of 5 degrees, or more preferably within a range of 2 degrees of being transverse to this direction.

In the illustrated example the interior face of the instrument interface elements and the front and rear faces of the drive assembly interface elements are parallel to one another. This can assist in the transferral of drive between the elements.

On engagement of the instrument interface 500 with the drive assembly interface 400, the drive assembly interface elements are held captive by respective instrument interface elements. The instrument interface elements and the drive assembly interface elements are all displaceable in the same direction. This direction is parallel to both the longitudinal axis 413 of the terminal link of the robot arm 404 and the longitudinal axis 512 of the instrument shaft 501.

Thus, in the illustrated example, linear drive is transferred between the drive assembly 400 and the instrument. In other examples, the drive need not be linear drive. For instance, the drive could be rotational drive, or drive about an arc.

During an operation or surgical procedure, the surgical robot is shrouded in a sterile drape to provide a sterile barrier between the non-sterile surgical robot and the sterile operating environment. The portion of the robot that is covered by the drape then need not be sterile. The surgical instrument is sterilised before being attached to the surgical robot. The sterile drape is typically constructed of a plastic sheet, for example made of polyester, polypropylene, polyethylene or polytetrafluoroethylene (PTFE). Suitably, the drape is flexible and/or deformable. This can assist in the drape shrouding the robot arm without interfering in the location and/or movement of the robot arm and/or instruments during the surgical procedure.

The sterile drape suitably passes between the drive assembly interface 400 and the instrument interface 500. The sterile drape forms a barrier between the drive assembly and the instrument interface. This barrier need not be completely hermetic, but is suitably substantially hermetic.

To effect the transfer of drive between the drive assembly interface 400 and the instrument interface 500, a drive transfer element is provided for engaging with both the drive assembly interface element and the instrument interface element. Where a plurality of drive assembly interface elements and/or instrument interface elements is provided, a corresponding plurality of drive transfer elements is provided. Suitably a drive transfer element is provided to transfer drive from each drive assembly interface element to a respective instrument interface element.

The drive transfer element comprises a first portion engageable with the robot arm. For example, the first portion is engageable with the drive assembly interface, such as being engageable with at least a portion of the drive assembly interface element. In the example illustrated in FIG. 4, the drive assembly interface element comprises a protrusion. The first portion suitably comprises a recess engageable with the protrusion of the drive assembly interface element. In other examples the drive assembly interface element can comprise a recess. In this case the drive transfer element suitably comprises a protrusion engageable with the drive assembly interface element recess.

The drive transfer element comprises a second portion engageable with the instrument. For example, the second portion is engageable with the instrument interface, such as being engageable with at least a portion of the instrument interface element. In the example illustrated in FIG. 5, the instrument interface element comprises a recess. The second portion suitably comprises a protrusion engageable with the recess of the instrument interface element. In other examples, the instrument interface element can comprise a protrusion. In this case the drive transfer element suitably comprises a recess engageable with the instrument interface element protrusion.

More generally, the first portion of the drive transfer element comprises one of a recess and a protrusion for engaging with a corresponding protrusion or recess of the drive assembly interface element. The second portion of the drive transfer element comprises one of a recess and a protrusion for engaging with a corresponding protrusion or recess of the instrument interface element.

A motion feedthrough can comprise the drive transfer element. Where a plurality of drive transfer elements are provided, the motion feedthrough can comprise the plurality of drive transfer elements. The motion feedthrough is suitably attachable to the drape. In other examples the drape can comprise the motion feedthrough.

Suitably, where the drape comprises a hole through which the drive assembly interface element and instrument interface element are engageable with one another, the motion feedthrough is provided to cover the hole. In some examples, the motion feedthrough is provided adjacent the hole, and the capturing of the motion feedthrough and/or the drape between the drive assembly interface and the instrument interface permits the motion feedthrough to substantially close the hole. The closing of the hole in the drape by the motion feedthrough permits maintenance of a hermetic, or at least substantially hermetic barrier between the drive assembly interface and the instrument interface.

In other examples, the motion feedthrough is attachable to the drape. For example, the motion feedthrough can be attached to the drape so as to close, or at least substantially close, the hole in the drape. For example, the periphery of the hole can be attached to the motion feedthrough, such as to a periphery of the motion feedthrough.

Suitably the motion feedthrough, or at least a portion of the motion feedthrough, for example the drive transfer element, is configured to move relative to a bulk portion of the drape. The motion feedthrough may comprise a plurality of cooperating portions that are configured to move relative to the bulk portion of the drape. The cooperating portions suitably cooperate with at least one other cooperating portion to another side of the drape material.

As mentioned, the provision of a compact drive transfer element can enable the interface to be reduced or minimised in at least one of length, width and depth. It can also permit a smaller and/or lighter interface which can allow the provision of a more highly dextrous system. A relatively less complex drive transfer element, motion feedthrough, and/or drape (including a motion feedthrough/one or more drive transfer element where provided as part of the drape) is also desirable as this can increase the ease of manufacture and/or reduce the cost of manufacture of the drape, which is typically a disposable item. The use of fewer parts in forming the drive transfer element and/or motion feedthrough may also reduce the number of joins or potential fluid paths from one side of the drape to the other, thereby helping to maintain a sterile barrier.

Figure 6A:
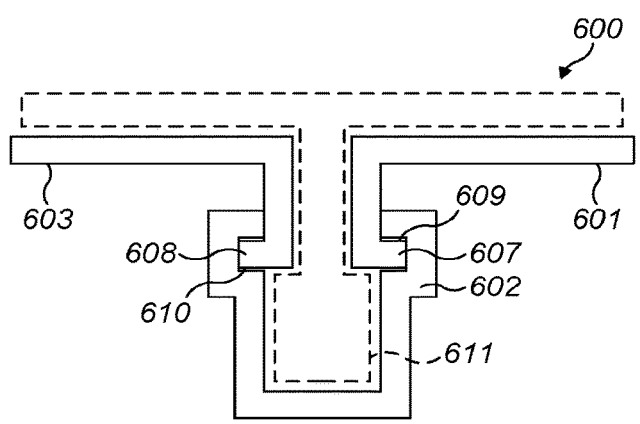
FIGS. 6a and 6b illustrate a motion feedthrough.

An example of a motion feedthrough 600 is illustrated in FIG. 6. The motion feedthrough comprises three drive transfer elements, each of which comprises a longitudinally extending element 601, 602, 603. In this example three elements are shown, corresponding to three drive assembly interface elements. In other configurations, the provision of more or fewer elements is possible. Generally, the number and/or arrangement of the elements will correspond to the number and/or arrangement of drive assembly interface elements.

The drive transfer elements 601, 602, 603 interface between the instrument interface elements and the drive assembly interface elements. In other words, a first portion, for example one side, of each element will interface with a respective drive assembly interface element and a second portion, for example another side, of each element will interface with a respective instrument interface element. Thus the one side and the other side will comprise one of a protrusion and a recess for engaging with a respective one of the drive assembly interface element and the instrument interface element.

In this manner the drive transfer elements 601, 602, 603 can be driven, for example linearly, together with the drive assembly interface elements.

Each drive transfer element is configured to engage with at least one other drive transfer element. A first drive transfer element 601 is engageable with a second drive transfer element 602. The second drive transfer element 602 is also engageable with a third drive transfer element 603. In the illustrated example the engagement between the first and second drive transfer elements 601, 602 and the engagement between the second and third drive transfer elements 602, 603 is similarly configured. This need not be the case.

Referring to FIG. 6, the first and second drive transfer elements 601, 602 engage by way of a tongue and groove engagement. The first and second drive transfer elements 601, 602 are configured to slidably engage with one another. The second and third drive transfer elements 602, 603 are configured to slidably engage with one another. In this way the drive transfer elements assist in maintaining a barrier. The barrier restricts the movement of fluid from one side of the barrier to the other. The barrier assists in the maintenance of the sterile barrier provided by the drape.

Figure 6B:
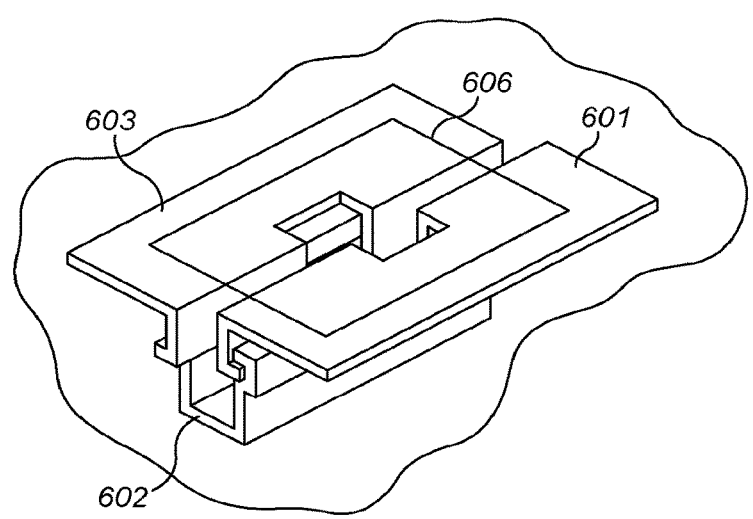

As illustrated in FIG. 6b, there is a gap in the material of the drape (an inner edge of this gap is shown at 606). This gap permits engagement of the drive transfer elements 601, 602, 603 with one of the drive assembly interface elements and the instrument interface elements. The gap is sized such that the instrument interface will cover the gap when the instrument is coupled to the robot arm. This assists in maintaining the sterile barrier.

In the illustrated example, a first tongue 607 on the first drive transfer element 601 and a second tongue 608 on the third drive transfer element 603 engage with respective grooves 609, 610 on the second drive transfer element. In other configurations the tongue can be provided on the second drive transfer element and the groove on the first and/or third drive transfer element. Combinations of such arrangements are also possible.

In some examples, a plug 611 is provided for locating at least partly within a recess formed between the first and third drive transfer elements 601, 603 and within the second drive transfer element 602. The provision of the plug 611 further restricts the ability of fluid to pass between the drive transfer elements and so enhances the barrier provided. The plug 611 is configured to slide within the recess so as not to restrict the relative movement between the drive transfer elements. For example, the plug 611 is made from a low friction material such as PTFE.

Figure 7A:
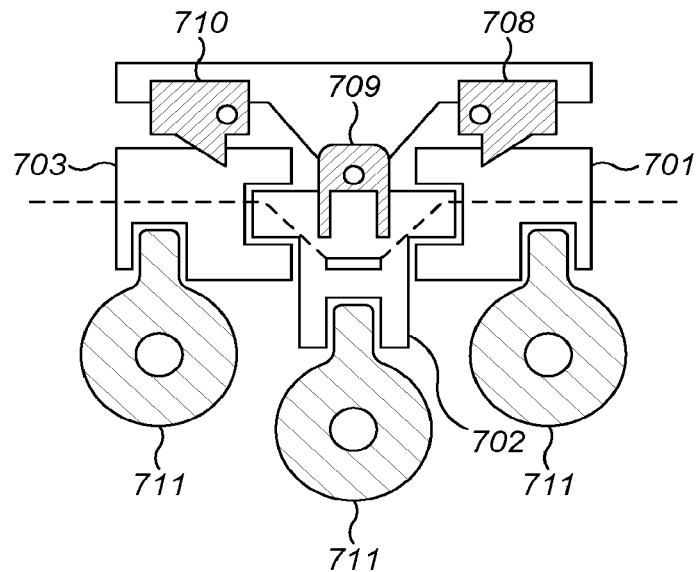
FIGS. 7a and 7b illustrate another motion feedthrough.
Figure 7B:
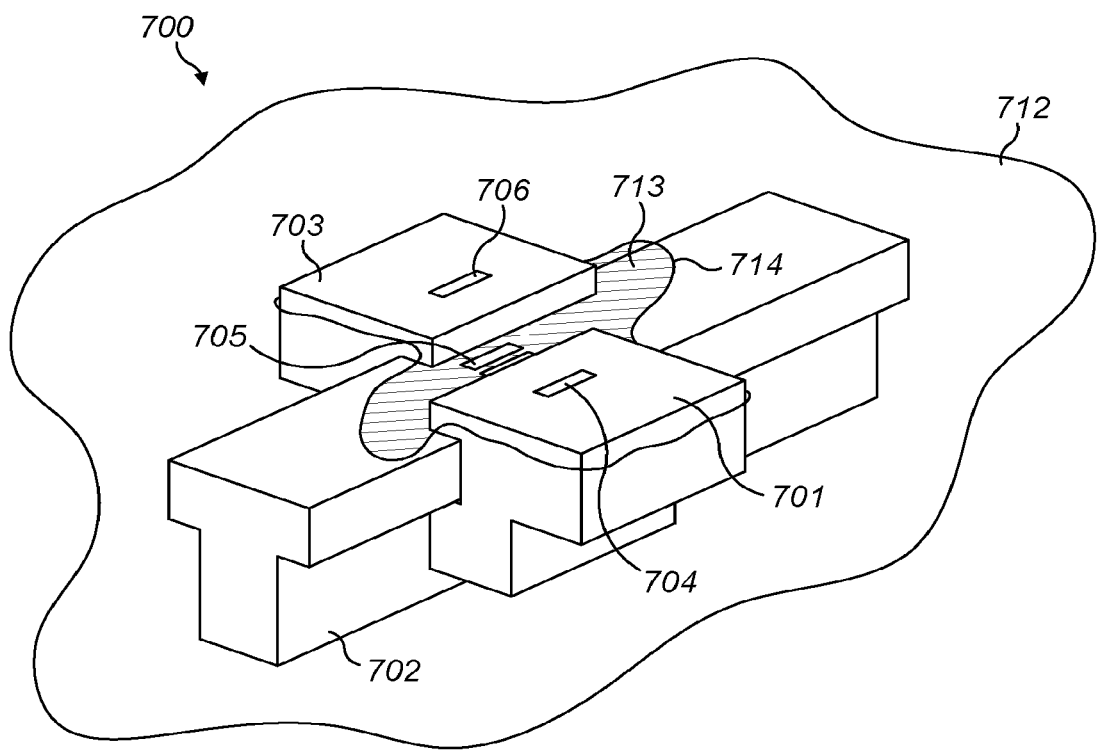

In another example, illustrated in FIGS. 7a and 7b, a motion feedthrough 700 comprises a first drive transfer element 701, a second drive transfer element 702 and a third drive transfer element 703. The first drive transfer element 701 engages by way of a tongue and groove engagement with the second drive transfer element 702. The third drive transfer element 703 engages by way of a tongue and groove engagement with the second drive transfer element 702. The first drive transfer element 701 comprises a first recess 704 on an upper surface (in the orientation of FIG. 7b). Similarly, the second drive transfer element 702 comprises a second recess 705 (in fact, a pair of recesses in the illustrated example, though there need not be two) on an upper surface. The third drive transfer element 703 comprises a third recess 706 on an upper surface.

The first, second and third recesses 704, 705, 706 are engageable with respective fins or protrusions of instrument interface elements. A first instrument interface element comprises a first fin 708, a second instrument interface element comprises a second fin 709 and a third instrument interface element comprises a third fin 710. The first fin 708 is engageable with the first recess 704. The second fin 709 is engageable with the second recess 705. The third fin 710 is engageable with the third recess 706. The first, second and third fins are movable within the instrument interface (i.e. in and/or out of the plane of FIG. 7a).

Three drive assembly interface elements are represented at 711. FIG. 7a shows a cross-sectional view through the motion feedthrough 700. In this example, the engagement between the drive transfer elements 703, 704, 705 and the drive assembly interface elements 711 is via a saddle-type engagement. Each drive transfer element engages in a recess of the drive assembly interface element, and the drive assembly interface element correspondingly engages in a recess of the drive transfer element.

As discussed above, the engagement between the drive assembly interface elements and the drive transfer elements, and between the drive transfer elements and the instrument interface elements can be achieved in any convenient manner. A protrusion on one can engage with a recess in the other.

Referring now to FIG. 7b, material of the drape 712 comprises a gap 713. The outer edge of the gap is shown at 714. The gap permits engagement of the fins with the recesses of the central drive transfer element 702. A portion of the periphery of the drape surrounding the gap or hole (i.e. that indicated at 714) is, in the illustrated example, attached to the drive transfer elements. The periphery of the drape around the gap is attached to portions of the first drive transfer element 701 to the side and facing away from the third drive transfer element 703. Similarly, the periphery of the drape around the gap is attached to portions of the third drive transfer element 703 to the side and facing away from the first drive transfer element 701. Thus as the first and/or the third drive transfer elements move, the material of the drape will also move. Thus the gap in the drape will move. In the illustrated example, the second drive transfer element 702 is longer than the first and the third drive transfer elements. This ensures that as the first and/or third drive transfer elements move, the gap in the drape is still effectively closed by the presence of the second drive transfer element.

Figure 8A:
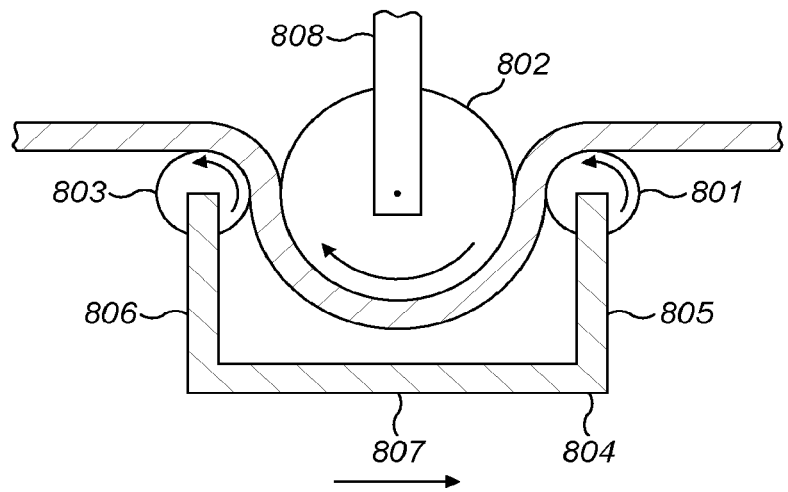
FIGS. 8a to 8c illustrate other motion feedthroughs.

Another example of a motion feedthrough is illustrated in FIG. 8a. In this example, the motion feedthrough comprises a plurality of capture members 801, 802, 803. The capture members define therebetween a capture portion. Suitably a pair of capture members define therebetween a capture portion. In one example, a first capture member 801 is provided adjacent a second capture member 802. The spacing between the first capture member and the second capture member is such as to retain a portion of drape material between the first and second capture members. Thus the drape is captured between the first and second capture members. The drape need not be held fast between the capture members. The drape can be guided between the capture members. The first and second capture members define therebetween a first capture portion. Suitably the drape can be controllably guided through the first capture portion.

The first capture member 801 can form at least a portion of one of the first or second portion of a drive transfer element. The second capture member 802 can form at least a portion of the other of the first or second portion of a drive transfer element.

In the illustrated example a second capture portion is defined between the second capture member 802 and a third capture member 803. Suitably the drape can be controllably guided through the second capture portion. As illustrated, the capture members can guide the drape over the first capture member 801, under the second capture member 802, and over the third capture member 803. In other examples, the capture members can be configured the other way round, so that the drape may pass under the first capture member, over the second capture member and under the third capture member.

The provision of three capture members in this way, rather than two capture members, permits a greater level of controllability of the material of the drape. It also permits the drape to enter and leave the motion feedthrough in a similar sense (i.e. over or under both of the first and the third capture members). This can assist in retaining the planarity of the drape as it passes through the motion feedthrough.

The first and third capture members 801, 803 are coupled together by a coupling structure 804 comprising a first limb 805 connectable to the first capture member 801, a second limb 806 connectable to the third capture member 803 and a third limb 807 connectable to each of the first and second limbs. The first and second limbs are of sufficient length that the second capture member 802 can extend into a recess defined by the coupling structure without the coupling structure interfering with the second capture member or the material of the drape passing against the second capture member. The coupling structure is suitably engageable with one of the drive assembly interface element and the instrument interface element. A fourth limb 808 is connectable to the second capture member 802. The fourth limb is suitably engageable with the other of the drive assembly interface element and the instrument interface element. Suitably the first portion of the drive transfer element comprises one of the coupling structure and the fourth limb. Suitably the second portion of the drive transfer element comprises the other of the coupling structure and the fourth limb.

As the drive assembly interface element is driven, the first or third capture member 801, 803 will push against the second capture member 802, or the second capture member will push against the first or third capture member (depending on whether the drive assembly interface element is engaged to the coupling structure 804 or to the fourth limb 808, and whether the drive assembly interface element is driven to the right or left) via the portion of the drape captured in the first capture portion or the second capture portion. Thus the first, second and third capture members will move together as the drive assembly interface element is driven.

As the motion feedthrough moves, the drape material need not move together with the motion feedthrough. Instead, the material can pass through the motion feedthrough. The material can flow through the first and the second capture portion. In this way, the material of the drape is not pulled taut as the drive assembly interface elements are driven. This arrangement therefore reduces strain on the drape, and can assist in maintaining the integrity of the sterile barrier.

At least one of the first, second and third capture members can comprise a low-friction material, such as PTFE. For example, the capture member can be formed of a low-friction material, or can comprise a low-friction material coating. This can assist in a smooth flow of the drape material past and/or over the respective capture members. At least one of the first, second and third capture members can comprise a roller pivotably mounted to a respective one of the first limb 805, the fourth limb 808 and the second limb 806. The roller is suitably configured to rotate so as to permit a smooth flow of material of the drape past and/or over the capture members as the motion feedthrough moves relative to the drape. Suitably one or more capture members is of a low-friction material and is configured to rotate.

In the illustrated example, as the coupling structure moves to the right in the orientation of FIG. 8*a*, as shown by the arrow under the coupling structure 804, the first capture member can rotate anticlockwise, the second capture member can rotate clockwise, and the third capture member can rotate anticlockwise.

In one example, the protrusion of the drive assembly interface element or of the instrument interface element comprises the second capture member, and the recess of the instrument interface element or of the drive assembly interface element comprises the first and third capture members.

Figure 8B:
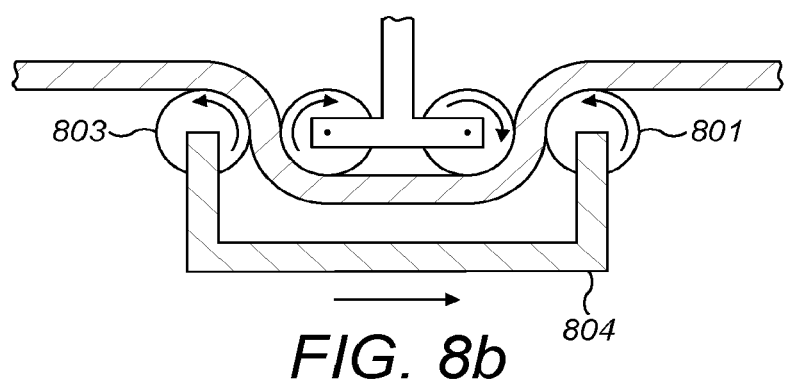

Another example of a motion feedthrough is illustrated in FIG. 8*b*. The second capture member is replaced with two spaced capture members. This configuration permits the motion feedthrough to have a smaller profile, thus saving space.

Figure 8C:
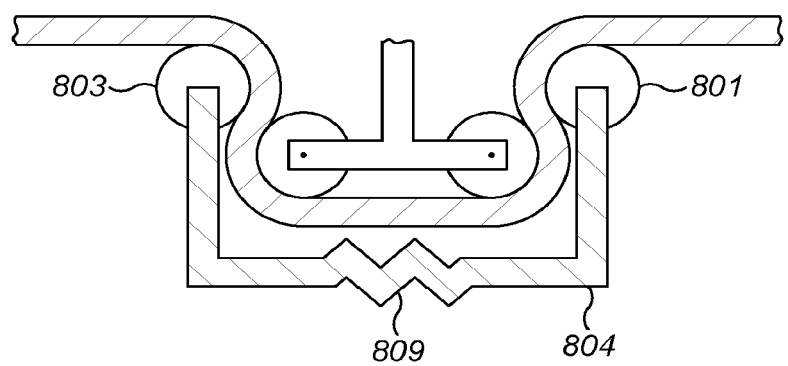

A further example is illustrated in FIG. 8*c*. In this example, the third limb 807 of the coupling structure 804 comprises a resilient and/or expandable section (schematically illustrated at 809). This resilient and/or expandable section permits the spacing between the first capture member 801 and the third capture member 803 to be varied. This enables the second capture member or (as illustrated) the two spaced capture members to extend within the recess defined by the coupling structure 804 by differing amounts, whilst the drape material is effectively retained within the first and second capture portions. As, for example, the two spaced capture members extend further into the recess of the coupling structure 804, the resilient and/or expandable section will contract such that the first capture member 801 and the third capture member 803 move closer to one another. The material of the drape will then take on a more pronounced S-shape as it passes through the first and second capture portions. This configuration provides for some tolerance in the relative positioning of the coupling structure 804 and the second capture member 802 (or the two spaced capture members). This configuration also permits this tolerance whilst maintaining a relatively consistent tension in the material of the drape.

Figure 9C:
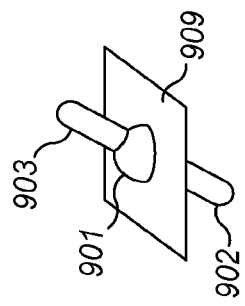
FIGS. 9a to 9f illustrate other motion feedthroughs.
Figure 9B:
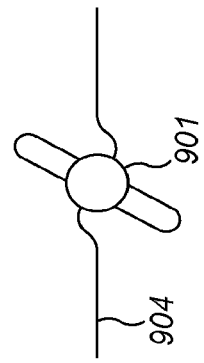
Figure 9A:
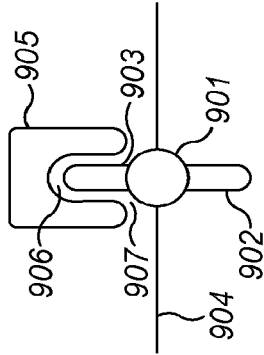

Referring now to FIG. 9*a*, in another example of a motion feedthrough, a hub 901 is provided in the drape, or attached to the drape. The hub is suitably generally spherically shaped, or generally cylindrically shaped, but other shapes are possible. The hub 901 comprises the first portion 902 and the second portion 903. The first portion 902 extends to one side of the drape 904 and the second portion extends to the other side of the drape 904. The first portion and the second portion are configured to move together with the hub. For example, the hub can be unitarily formed with one or both of the first portion and the second portion. As illustrated, the first portion and the second portion here comprise projections or pins which are engageable with corresponding recesses on the drive assembly interface element and the instrument interface element, but other engagement mechanisms are possible, as discussed above. An example of a recess on an instrument interface element is illustrated at 905. The recess comprises a channel 906 with an opening 907. Suitably the opening 907 is flared or widened to permit easier location of the second portion 903 within the channel 906. A similar recess can also be provided for receiving the first portion 902.

As the drive assembly interface element (not shown) is moved, it will cause movement of an end of the first portion 902 distal from the hub 901. This causes rotation of the hub about a central axis (for example an axis through a central point of a spherically shaped hub, or a longitudinal axis of a cylindrically shaped hub), and a corresponding movement in an opposite direction of a distal end of the second portion 903. This causes a corresponding movement of the instrument interface element comprising the recess 905. Movement of the drive assembly interface element and/or the instrument interface element can be linear or about an arc. Where the movement is linear, the distal ends of the first portion and/or the second portion will move relative to the end of the channel 906 in the recess as the hub 901 rotates. Thus the channel 906 is suitably long enough that such relative movement can be accommodated without the first and/or second portion thereby disengaging the drive assembly interface element or the instrument interface element respectively.

As the hub 901 rotates there will be a limited amount of wrinkling or buckling of the drape material adjacent the hub. Thus the drape is suitably resilient enough and/or baggy/loose enough to accommodate such buckling over the extent of rotation of the hub.

The rotation of the hub 901 is suitably constrained such that movement of the protrusions is restricted to a single plane. This can be achieved by providing a plate 909 in or attached to the drape as illustrated in FIG. 9*c*. The plate 909 suitably comprises a recess or cup for retaining the hub 901 so as to permit it to rotate in a single plane. For example, the hub can be mounted on an axle or rod about which it is permitted to rotate. The rod can be retained in a desired orientation in the plate 909.

Figure 9F:
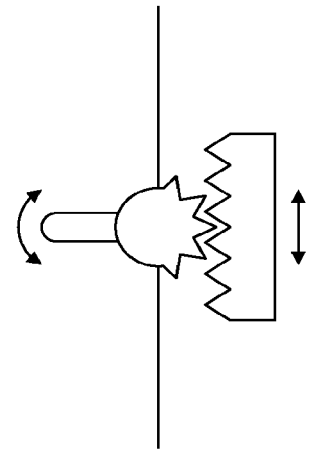
Figure 9E:
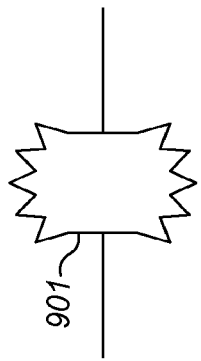
Figure 9D:
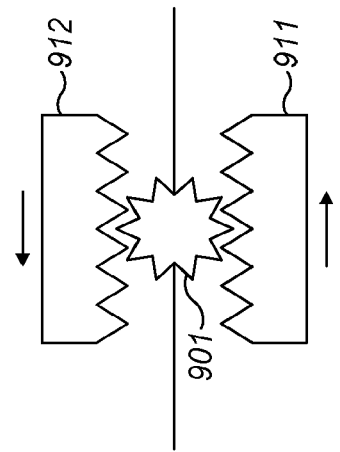

Referring now to FIGS. 9*d* and 9*e*, the first and/or the second portion can comprise at least a portion of a cog, or of a cog wheel. In other words, the first portion can comprise a plurality of sprockets and/or the second portion can comprise a plurality of sprockets. In the example illustrated in FIG. 9*d*, the drape material can be attached to a portion of the cog, for example to a particular sprocket. In the example illustrated in FIG. 9*e*, the hub comprises a portion without sprockets to which the drape is attachable.

Where the hub 901 comprises a portion of a cog, the corresponding one of the drive assembly interface element and the instrument interface element suitably comprises a rack. The sprockets on the cog are suitably engageable with the rack. Thus, as a rack to one side of the drape is moved, for example a first rack 911 (which might be coupled to or form part of a drive assembly interface element), the hub 901 will rotate, causing movement of the rack to the other side of the drape, for example a second rack 912 (which might be coupled to or form part of an instrument interface element). The two racks will move in opposite directions. Thus, as illustrated, as the first rack 911 moves to the right (in the orientation of FIG. 9*d*), the second rack 912 will move to the left.

The provision of a rack for engagement with the hub facilitates ease of location of the hub. The lateral positioning of the hub is not critical. This therefore provides for a greater tolerance in the engagement between the drive transfer element and one or both of the drive assembly interface element and the instrument interface element.

One of the first portion and the second portion can comprise a portion of a cog, and the other of the first portion and the second portion can comprise a protrusion. Such a configuration is illustrated in FIG. 9f. In this arrangement, linear movement of the rack results in rotation of the hub, causing movement of the protrusion about an arc. This can cause either linear movement or movement about an arc of, for example, an instrument interface element comprising a recess within which the protrusion is receivable. Thus linear movement can be translated to movement about an arc. This configuration permits flexibility in the construction of the motion feedthrough, allowing optimisation of the motion feedthrough in different circumstances.

The above examples in which a hub rotates rather than moves linearly may be particularly suitable for use in arrangements where the drape is tensioned, for example where it comprises a tensioned diaphragm. In such configurations it may be easier to rotate the hub, causing buckling in the drape, than it would be to move a portion of the drape laterally. Thus this arrangement can reduce the forces needed for effective motion feedthrough.

Figure 10A:
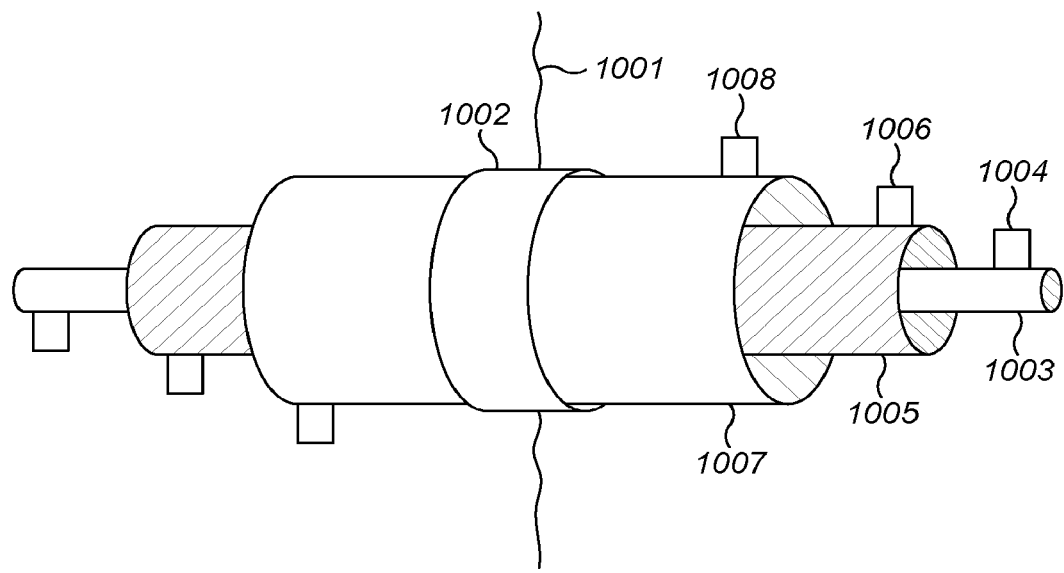
FIGS. 10a and 10b illustrate another motion feedthrough.
Figure 10B:
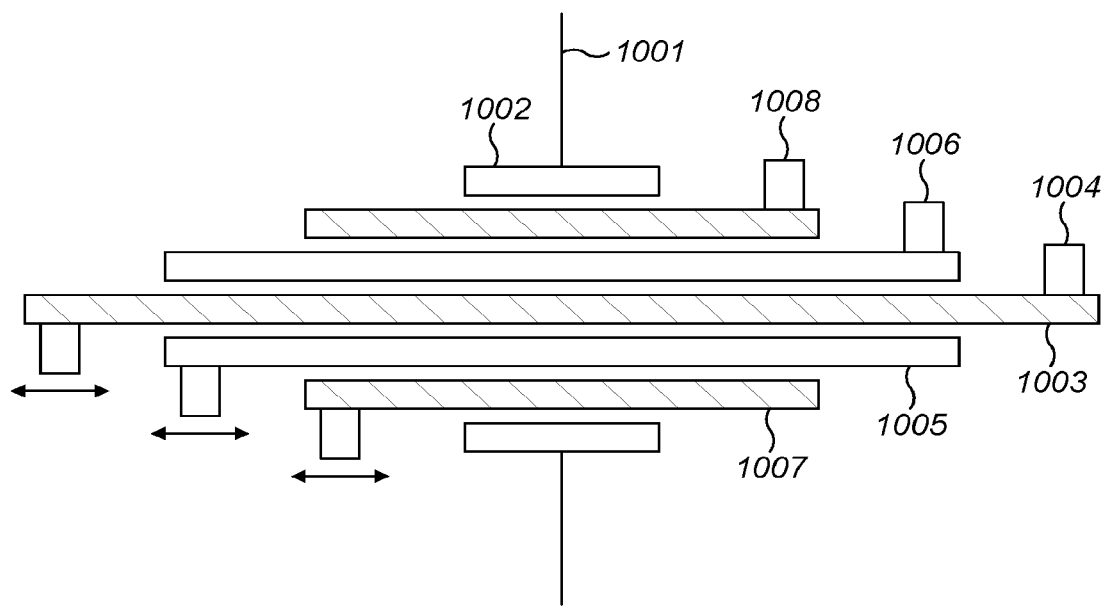

In another example of a motion feedthrough, illustrated in FIGS. 10a and 10b, the motion feedthrough comprises three concentric or nested elements, such as tubes, which are coupled to the drape 1001 via a clamp or O-ring 1002. The clamp or O-ring permits rotation of the outermost tube relative to the drape whilst maintaining the sterile barrier. In an alternative configuration, an additional tube surrounding the illustrated outer tube can be provided which can be clamped by the clamp. In this case the clamp or O-ring need not permit rotation of this additional tube. Suitably, where a clamp is provided, an O-ring is provided for sealing the join between the clamp and the drape. The O-ring is suitably an elastomer or a rubber. An O-ring may be provided between adjacent tubes, permitting sealing of the interface whilst permitting relative motion between the adjacent tubes. FIG. 10 is schematic; some of the dimensions have been exaggerated for ease of understanding. Each nested element can comprise a drive transfer element.

In the illustrated example, an innermost tube (or rod) 1003 is provided with or comprises an engagement portion 1004 which is engageable with one of the drive assembly interface element or the instrument interface element. The motion feedthrough comprises a middle tube 1005 surrounding the innermost tube. The middle tube 1005 is provided with or comprises an engagement portion 1006 which is engageable with another one of the drive assembly interface element or the instrument interface element. The motion feedthrough comprises an outer tube 1007 surrounding the middle tube 1005. The outer tube is provided with or comprises an engagement portion 1008 which is engageable with another one of the drive assembly interface element or the instrument interface element. In the illustrated example the engagement portions 1004, 1006, 1008 are schematically shown as protrusions, but the engagement portions need not be protrusions in all examples. Suitably the motion feedthrough comprises seals such as O-ring seals between the innermost tube 1003 and the middle tube 1005 and between the middle tube 1005 and the outer tube 1007.

The tubes extend to the other side of the drape 1001, and are similarly provided with, or comprise, engagement portions on the other side of the drape too. Thus a drive assembly interface element can engage with one of the tubes to one side of the drape, and an instrument interface element can engage with the same tube to the other side of the drape, permitting motion feedthrough through the drape.

The motion feedthrough can be at least one of linear motion and rotational motion. The linear motion is along the longitudinal axes of the tubes. The rotational motion is about the longitudinal axes of the tubes. The provision of both linear and rotational motion permits a larger number of types of motion, or control signals, to be passed through the drape by the motion feedthrough.

Suitably each tube extends beyond its next outermost tube or the clamp/O-ring by an amount sufficient to permit the whole range of linear movement of that tube without the engagement portion thereby interfering with the next outermost tube or the clamp/O-ring. In other words, the longitudinal path over which each engagement portion 1004, 1006, 1008 is linearly movable may be non-overlapping with the longitudinal path over which each other engagement portion is linearly movable.

The motion feedthrough illustrated in FIGS. 10a and 10b shows engagement portions 1004, 1006, 1008 on an upper side (in the orientation of the figures) of the tubes to one side of the drape, and on a lower side of the tubes to the other side of the drape. This need not be the case. The engagement portions can be located in any suitable location on the tubes, and in any suitable circumferential position.

It is convenient to provide the motion feedthrough with tubes so as to permit the transfer of rotational motion as well as linear motion. It is also possible for the tubes to have other shapes, which need not all permit the transfer of rotational motion. For example, the tubes can be non-circular in cross-section, for example oval or polygonal.

Figure 11A:
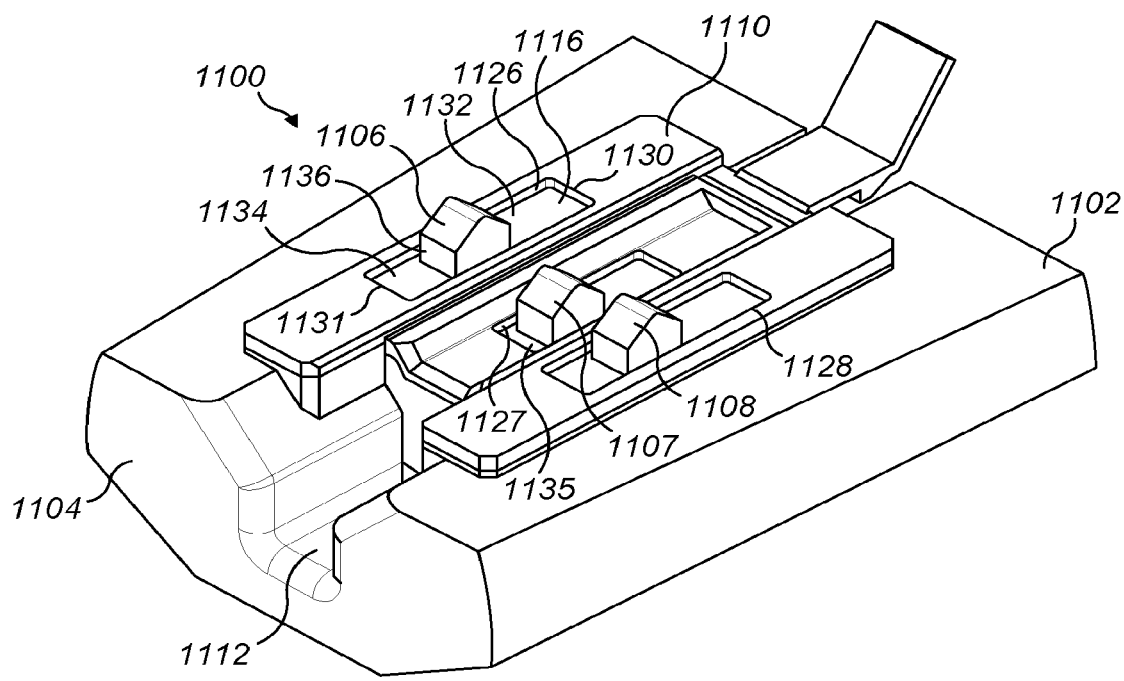
FIG. 11a illustrates one side of an interface structure.
Figure 11B:
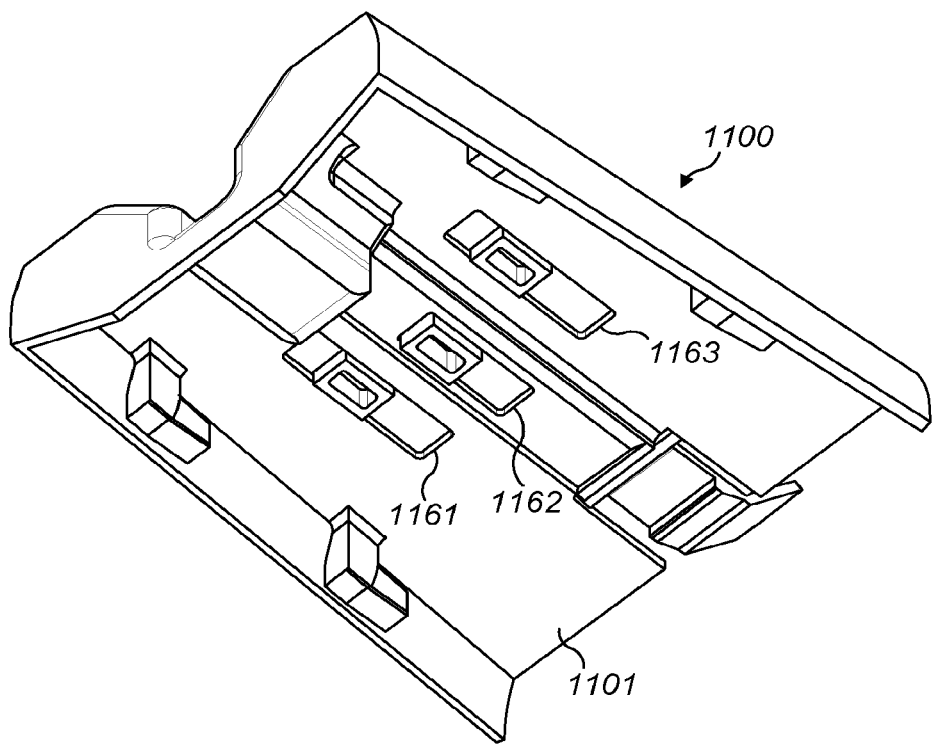

In some examples, the drape comprises an interface structure 1100 for interfacing between the drive assembly interface 400 and the instrument interface 500. A motion feedthrough can comprise the interface structure. FIGS. 11a and 11b show an exemplary interface structure 1100 in isolation. The interface structure 1100 may be integrally formed with the drape. Alternatively, the interface structure 1100 may be formed separately from the drape and subsequently attached to the drape. Either way, the interface structure 1100 is sterile. One side 1101 of the interface structure 1100 directly contacts the drive assembly interface. The other side 1102 of the interface structure 1100 directly contacts the instrument interface. Thus, the interface structure 1100 prevents the non-sterile drive assembly interface from directly touching the sterile instrument interface and hence maintains the sterile barrier between the two components.

The interface structure 1100 comprises a main body 1104 and drive transfer elements 1106, 1107, 1108. The drive transfer elements are movable relative to the main body. Conveniently, when the interface structure 1100 is attached to the surgical robot arm, the main body 1104 lies parallel to the surface(s) of the drive assembly interface 400. Suitably in this attached configuration, the main body 1104 is aligned with the drive assembly interface.

The main body 1104 comprises a first side 1101 which faces the robot arm when the instrument is attached to the robot arm. Specifically, the first side 1101 faces the drive assembly 400. The main body 1104 comprises a second side 1102 opposite to the first side. The second side 1102 faces the instrument when the instrument is attached to the robot arm. Specifically, the second side 1102 faces the instrument interface 500. Suitably both the first side 1101 and the second side 1102 are substantially flat. The first side and the second side need not be completely flat. Being substantially flat, or flat over at least a portion of its surface (for example over at least 10% of its surface, over at least 20% of its surface, over at least 30% of its surface, preferably over at least 40% of its surface or more preferably over at least 50% of its surface) permits the interface structure 1100 to be compactly sandwiched between the instrument and the robot arm when the instrument is attached to the robot arm.

Being flat can include having flat portions in different planes. For example, as illustrated in FIG. 4, the drive assembly interface 400 can have portions which are flat, but disposed generally over two planes, as described above. Suitably the interface structure 1100 is configured to correspond to the general surface features of the drive assembly interface so as to compactly engage therewith, reducing or minimising gaps or space between the interface structure and the drive assembly interface.

The main body 1104 comprises an aperture. In the interface structure 1100 illustrated in FIGS. 11a and 11b, an aperture is located generally central to the main body 1104, though it need not be located in this position. In the illustrated example, the main body 1104 comprises three apertures: a first aperture 1161, a second aperture 1162 and a third aperture 1163. The apertures provide for communication between the first side 1101 and the second side 1102 though the main body 1104.

A cover 1110 is provided which covers a portion of the main body 1104. The cover covers the part of the main body that comprises the apertures. In the illustrated implementation, the cover 1110 is located on the second side 1102 of the main body 1104. In other examples, the cover can be located on the first side 1101 of the main body, or covers can be located on both sides of the main body. The cover 1110 is attached to the main body 1104. Suitably the cover 1110 is fixed to the main body 1104. The cover can be attached to the main body by adhesive, or by any other convenient means or method of attachment.

The cover 1110 comprises further apertures, or slots. In the illustrated example, the cover 1110 comprises a first slot 1126, a second slot 1127 and a third slot 1128. The slots communicate with the apertures in the main body 1104. The first slot 1126 is aligned with the first aperture 1161; the second slot 1127 is aligned with the second aperture 1162; the third slot 1128 is aligned with the third aperture 1163. Thus the slots in the cover 1110 provide fluid flow paths between the first side and the second side 1102 of the main body.

The apertures in the main body 1104 define paths along which the drive transfer elements are movable. In the example illustrated in FIGS. 11a and 11b, the paths are linear paths. The first aperture 1161 defines a first path; the second aperture 1162 defines a second path; the third aperture 1163 defines a third path.

The main body 1104 and the cover 1110 define therebetween channels along which drive transfer elements are movable. Suitably the drive transfer elements are slideable within the channels. A lip adjacent an aperture in the main body 1104 and a corresponding lip adjacent an aperture in the cover 1110 define a channel between the lips. The main body 1104 and the cover 1110 define two channels per aperture, one to either side of the aperture. The channels extend along the length of the apertures.

As mentioned above, the interface structure 1100 comprises drive transfer elements. In the example illustrated in FIGS. 11a and 11b, the interface structure comprises three drive transfer elements: a first drive transfer element 1106, a second drive transfer element 1107 and a third drive transfer element 1108. The first drive transfer element 1106 is slidably received in the first slot 1126. The second drive transfer element 1107 is slidably received in the second slot 1127. The third drive transfer element 1108 is slidably received in the third slot 1128. Each drive transfer element is slidably movable along its respective slot.

The drive transfer elements comprise a central portion and an extending portion which extends away from the central portion. With reference to the first drive transfer element 1106, the central portion 1136 comprises a protrusion. The extending portion 1116 comprises a flat plate that extends from the central portion 1136. The extending portion 1116 is elongate in two opposite directions which, when the first drive transfer element 1106 is located in the first slot 1126, are aligned with the directions in which the first slot 1126 extends. In directions transverse to these directions, i.e. in directions transverse to the extent of the slots, the first drive transfer element comprises a first lip. The first lip is receivable into channels to either side of the first aperture 1161. Similarly, a second lip on the second drive transfer element 1107 is receivable into channels to either side of the second aperture 1162. A third lip is receivable into channels to either side of the third aperture 1163. Suitably the drive transfer elements are rigid.

The drive transfer elements extending along the slots restricts the fluid flow path through the apertures. The drive transfer elements extending into the channels adjacent the apertures restricts the fluid flow path through the apertures. In this way the drive transfer elements restrict the fluid flow path around the drive transfer elements.

Suitably the inter-engagement between the drive transfer elements 1106, 1107, 1108 and the main body 1104 is such as to restrict the fluid flow path between the drive transfer elements and the main body. This inter-engagement is, for example, by a portion of the drive transfer elements being retained adjacent the main body, such as by being retained in the slots, or by being retained in the channels.

The first slot 1126 comprises a first end 1130 and a second end 1131 opposite the first end, along the length of the first slot. The extending portion 1116 of the first drive transfer element 1106 comprises a first extension 1132 and a second extension 1134. The length of the first extension 1132 from the central portion 1136 of the first drive transfer element 1106 is L1. The length of the second extension 1134 from the central portion 1136 of the first drive transfer element 1106 is L2.

At the furthest extent of movement of the first drive transfer element 1106 towards the second end 1131 of the first slot 1126, the distance between the central portion 1136 and the first end 1130 is D1. At the furthest extent of movement of the first drive transfer element 1106 towards the first end 1130 of the first slot 1126, the distance between the central portion 1136 and the second end 1131 is D2.

The length of the first extension L1 is at least the same as the distance D1. Suitably L1 is greater than D1, for example to provide an overlap between the first extension and the main body and/or between the first extension and the cover. The length of the second extension L2 is at least the same as the distance D2. Suitably L2 is greater than D2, for example to provide an overlap between the first extension and the main body and/or between the first extension and the cover. In this way, the extending portion 1116 (comprising the first extension 1132 and the second extension 1134) covers the aperture. In other words, it covers the space between the central portion and the ends of the slots. Providing the extension portions 1132, 1134 to be the same length as, or greater than, the potential gap means that the gap will remain covered throughout the extent of movement of the drive transfer element within the slot.

The second drive transfer element 1107 and the third drive transfer element 1108 are similarly configured. For example, the second drive transfer element 1107 comprises a third extension 1135. Thus each aperture or slot remains covered throughout the whole extent of movement of the respective drive transfer element.

Referring to FIGS. 11*a* and 11*b*, the slots are not all of equal length. The second slot 1127 is shorter than the first slot 1126 and the third slot 1128. The slots need not be sized in this particular way. Each slot can be sized as desired to account for or permit the required movement of the respective drive transfer element. In this example the central drive assembly interface element 402 is configured to move along a shorter linear path 410 than the linear paths 409, 411 along which the left-hand drive assembly interface element 401 and the right-hand drive assembly interface element 403 are configured to move. Correspondingly the first slot 1126 and the third slot 1128 are longer than the second slot 1127. In the illustrated example the first drive transfer element and the third drive transfer element have a relative movement with respect to the main body of ±5.1 mm (i.e. 10.2 mm from one end to the other). The second drive transfer element has a relative movement with respect to the main body of ±3 mm (i.e. 6 mm from one end to the other). The relative movements need not be the same as these. In some examples the relative movement of the first and third drive transfer elements is longer or shorter than this. The relative movement of the second drive transfer element can be longer or shorter than this. The ratio of relative movements need not be this ratio, but could be greater or less than this ratio.

The ends of the slot in the cover are further apart than the ends of the aperture in the main body. The slot in the cover is longer than the respective aperture in the main body. This additional length permits the socket 502 to protrude at least partially within the slot in the cover without reducing the travel of the drive transfer element within the aperture. Suitably the additional length of the slot compared to the aperture is at least equal to the width of that portion of the socket disposed between the drive transfer element and the end of the slot. Suitably the additional length of the slot compared to the aperture is at least equal to twice the width of that portion of the socket disposed between the drive transfer element and the end of the slot, so as to avoid reducing the travel of the drive transfer element within the aperture at either end of the range of movement.

The protrusion of the socket 502 at least partially within the slot in the cover permits better coupling between the socket and the drive transfer element. The protrusion of the socket at least partially within the slot in the cover permits better coupling between the socket and the fin. The coupling is improved by providing a greater overlap between the socket and the fin in the direction of drive transfer.

In the illustrated example the slots are aligned at one end. An end of the first slot proximal to an indent 1112 in the interface structure 1100 is aligned with an end of the second slot proximal to the indent 1112 and an end of the third slot proximal to the indent 1112. When the drive transfer elements are moved, for example by being driven, to their furthest extent towards the indent 1112, each of the drive transfer elements will be aligned with the others. Where the ends of the slots, or the drive transfer elements, are aligned, they may be at the same distance as one another along a length of the interface structure.

In other examples, the length of the slots need not match the length of the linear paths. Suitably the slots are at least as long as the linear paths.

This arrangement assists in restricting fluid flow through the aperture or slot. Restricting this fluid flow assists in maintaining a sterile barrier. Thus when attached to a surgical robot arm, and/or to a surgical instrument, the interface structure can assist in maintaining the sterile barrier between the arm and the instrument.

As mentioned above, the central portion 1136 of the first drive transfer element 1106 comprises a protrusion to the second side 1102 of the interface structure 1100. As can be seen from FIG. 11*a*, each of the drive transfer elements comprises a central portion which comprises a protrusion to the second side 1102 of the interface structure 1100. In this example, the central portions of the drive transfer elements comprise recesses to the first side 1101 of the interface structure 1100 (visible in FIG. 11*b*) for engagement with the fins of the respective drive assembly interface elements.

In other examples, the central portions of the drive transfer elements can be arranged the other way round. In other words, recesses can be provided towards the second side and protrusions can be provided towards the first side. Alternatively, any combination of protrusions and recesses can be provided. This can include one drive transfer element comprising either both a protrusion towards the first side and a protrusion towards the second side, or a recess towards the first side and a recess towards the second side. The configuration adopted will suitably match that of the drive assembly interface 400 and the instrument interface 500.

Suitably the drive transfer elements comprise a plastic material. Preferably the drive transfer elements are able to deform slightly so as to accommodate interfacing with the drive assembly interface elements and/or the instrument interface elements. Preferably the drive transfer elements engage with the drive assembly interface elements by an interference fit, such as a light interference fit. Suitably the drive transfer elements engage with the instrument interface elements by an interference fit, such as a light interference fit.

Generally, each drive transfer element comprises a first portion and a second portion. The central portion suitably comprises the first portion and the second portion.

Referring to the illustrated example, the first portion comprises a recess and the second portion comprises a protrusion. The protrusion of the second portion comprises a chamfer and/or rounded edge to ease engagement of the protrusion with a cup, such as a cup on an instrument interface element, into which the protrusion is receivable. In the illustrated example, as best seen from FIG. 11*a* the protrusion of the second portion has a V-shape in cross-section. This aids in engaging the protrusion with the cup. The V-shape of the protrusion can accommodate misalignment between the protrusion and the cup as the instrument is attached to the interface structure. The recess of the first portion comprises a flared and/or rounded edge adjacent the opening into the recess to ease engagement with a protrusion or fin, such as a protrusion or fin on a drive assembly interface element, with which the recess is engageable.

Preferably, the first portion and the drive assembly interface element comprise cooperating surfaces which are complementary to one another. Preferably, the second portion and the instrument interface element comprise cooperating surfaces which are complementary to one another.

The main body 1104 of the interface structure 1100 is rigid in the illustrated example. In other examples it need not be rigid. At least a portion of the main body 1104 can be of a resilient and/or deformable material. At least a portion of the main body can be flexible. A portion of the main body can be a flexible material such as a fabric. A portion of the main body can be unconstrained. The resilience, flexibility and/or unconstrained nature of the portion of the main body can permit and/or accommodate relative movement between the drive transfer elements.

Suitably a portion of the main body between the apertures is resilient and/or deformable, for example flexible. Suitably the main body can be formed in whole or in part of a resilient and/or deformable material. The resilient and/or deformable material can comprise one or more of silicone, latex, vinyl, butyl, nitrile, neoprene, and a polymer. The resilient and/or deformable material suitably comprises a material with a low modulus and low hysteresis. The resilient and/or deformable material suitably comprises a material with a good strain to failure.

In another example, illustrated schematically in FIG. 12, the interface structure comprises one or more movable portions 1210. The movable portion is flexible and/or elastic. For example, the movable portion is a material such as a fabric. Preferably the material is water-resistant to assist in providing the sterile barrier between the robot arm and the instrument. The material can be constructed of a plastic sheet, for example made of polyester, polypropylene, polyethylene or polytetrafluoroethylene (PTFE). The movable portion 1210 reduces the likelihood that the material of the interface structure ruckles and/or controls the extent to which the material of the interface structure ruckles, though it need not do this in all examples. The movable portion is arranged to control the manner in which material of the interface structure moves as the drive transfer elements 1201, 1202, 1203 move. This can permit control of, and/or reaction to, the tension within the material of the interface structure.

The first portion and/or the second portion is attached to the movable portion. In other examples, the first portion can be attached to one movable portion. The second portion can be attached to another movable portion. The flexible and/or elastic nature of the movable portion can assist in accommodating movement of the first and/or the second portions relative to the main body.

In the illustrated example, two reels 1211, 1212 are provided. Each reel is configured to hold and retain an amount of material. Material can be rolled onto one or both reels to take up slack in the material between the reels. Material can be rolled off one or both reels to relieve tension in the material between the reels. Material can be rolled onto or off the reels to accommodate movement of the drive transfer elements.

Figure 12A:
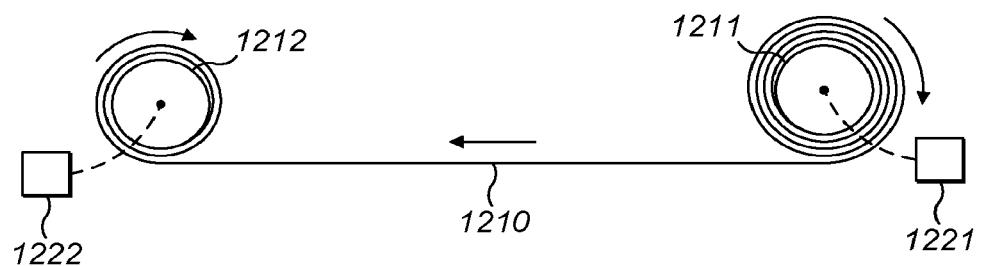
FIG. 12a schematically illustrates a side view of an alternative interface structure.

Referring to FIG. 12a, the material between the reels moves to the left. This is, for example, because the drive transfer element attached to that material (not shown) is driven to the left by the drive assembly. As a drive assembly interface element to which that drive transfer element is engaged moves to the left, so will the material held by the drive transfer element. The right-hand reel 1211 will rotate clockwise, as indicted by the arrow, to feed material from the right-hand reel 1211. This means that material between the drive transfer element and the right-hand reel 1211 is not exposed to a high tension that might otherwise cause a rupture in the material, and/or disrupt operation of the interface structure and/or the instrument interface. The left-hand reel 1212 can rotate anti-clockwise, as indicated by the arrow, to roll material onto the left-hand reel 1212. This means that material between the drive transfer element and the left-hand reel 1212 does not become loose. Similarly, if the drive transfer element moves to the right, material will be fed from the left-hand reel 1212. Material can be taken up by the right-hand reel 1211. Either or both of the left-hand reel 1212 and the right-hand reel 1211 need not take up slack in the material. However, maintaining the material taut can assist in covering the aperture and in maintaining the sterile barrier.

Figure 12B:
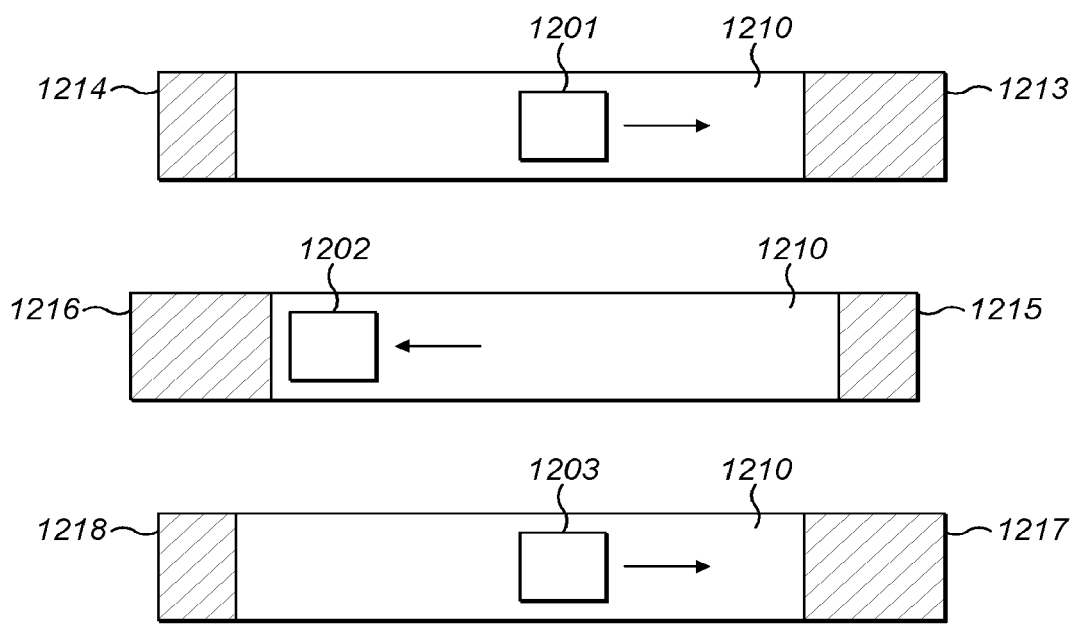

Referring now to FIG. 12b, where three drive transfer elements 1201, 1202, 1203 are provided adjacent one another, three pairs of reels are provided. This permits each of the three drive transfer elements to move independently of one another without such independent movement causing tension to increase in the material of the interface structure. For example, the provision of a pair of reels for each drive transfer element can reduce the extent to which the material between the reels, i.e. the movable portion, is exposed to tension, shear forces and/or rupture. This may be compared to an arrangement in which a single pair of reels is provided for a plurality of drive transfer elements, and the positioning of the material is based, for example, on an average such as a weighted average of the positions of the plurality of drive transfer elements.

In the illustrated example, an uppermost (in the orientation of FIG. 12b) drive transfer element 1201 is moved to the right (as indicated by the arrow), a middle drive transfer element 1202 is moved to the left (as indicated by the arrow) and a lower drive transfer element 1203 is moved to the right (as indicated by the arrow). A first right-hand reel 1213, that of the uppermost section, takes up material of the movable portion and so has a greater reel diameter. A first left-hand reel 1214, that of the uppermost section, feeds material of the movable portion from the reel and so has a smaller reel diameter. A second right-hand reel 1215, that of the middle section, feeds material of the movable portion from the reel and so has a smaller reel diameter. A second left-hand reel 1216, that of the middle section, takes up material of the movable portion and so has a greater reel diameter. A third right-hand reel 1217, that of the lower section, takes up material of the movable portion and so has a greater reel diameter. A third left-hand reel 1218, that of the lower section, feeds material of the movable portion from the reel and so has a smaller reel diameter.

It will be understood that where the number and/or arrangement of the drive transfer elements differs from the illustrated example, the number and/or arrangement of the pairs of reels can similarly differ.

Provision of a reel can assist in reducing the length of the interface structure compared to provision of rigid drive transfer elements. Provision of a reel can ensure that the sterile barrier is maintained whilst reducing the length of the interface structure needed. This is because the reel can take up material that might otherwise have projected past (overlapped) the end of the slot when the central portion is adjacent that end of the slot.

Material of the interface structure, such as the movable portion, can be taken up and/or fed from a reel by driving the respective reel about its axis. Material of the interface structure can be taken up and/or fed from a reel by resiliently biasing the respective reel about its axis. In one example each reel is resiliently biased and is also driven.

Resiliently biasing a reel can assist in keeping tension within the material of the interface structure consistent. When tension is lowered (by, for example, a drive transfer element moving towards the relevant reel), the biasing of the reel will cause the reel to rotate so as to take up material. When tension is increased (by, for example, a drive transfer element moving away from the relevant reel), the biasing of the reel will permit the reel to rotate to as to feed material from the reel.

The resilience of the resilient biasing can be determined to provide for a desired tension or range of tension in the material of the interface structure. The resilient biasing is, in one example, provided by a spring coupled to the respective reel.

Driving of the reels can be accomplished by coupling a motor, such as an electric motor, to each reel. Driving the reels can permit tension to be released and/or slack taken up at a desired speed. For example, driving the reels can permit tension to be released and/or slack taken up at a higher speed than might occur with resilient biasing. Driving the reels can permit tension to be controlled more accurately than by relying on resilient biasing, or on resilient biasing alone.

In one example, one of a pair of reels is coupled to a motor for driving that reel, and the other of the pair of reels is resiliently biased. The resilient biasing adapts to the tension in the material whilst the motor is driven so as to achieve a desired tension. This arrangement permits control of the tension in the material of the interface structure.

A first tension sensor 1221 (shown schematically in FIG. 12*a*) is coupled to the right-hand reel 1211, 1213, 1215, 1217. The first tension sensor is configured to sense tension in the material between the drive transfer element and the right-hand reel. The first tension sensor is suitably coupled to a rotational axis of the right-hand reel. A second tension sensor 1222 (shown schematically in FIG. 12*a*) is coupled to the left-hand reel 1212, 1214, 1216, 1218. The second tension sensor is configured to sense tension in the material between the drive transfer element and the left-hand reel. The second tension sensor is suitably coupled to a rotational axis of the left-hand reel. Tension sensed by either or both of the first tension sensor and the second tension sensor is used to determine how to drive either or both of the right-hand reel and the left-hand reel. In other words, either or both of the right-hand reel and the left-hand reel is controlled in dependence on tension sensed by either or both of the first tension sensor and the second tension sensor.

The provision of the first tension sensor and the second tension sensor can permit a comparison of the tension sensed by each of the first and second tension sensors. This comparison can be used to detect rupture or other damage in the material. For example, if the tension sensed at both of a pair of reels reduces as a drive transfer element moves, it can be determined that the material between the reels has ruptured.

In some examples, only one tension sensor need be provided for each of a pair of reels.

In the foregoing, motion feedthroughs and drive transfer elements have been discussed that can accommodate three linearly moving drive assembly interface elements which are generally arranged adjacent one another. An illustration of this general arrangement is given in FIG. 13*a*. Part of a drive assembly interface 1300 is shown in FIG. 13*a*. The drive assembly interface 1300 comprises three drive assembly interface elements 1304, 1305, 1306 which are configured to be movable along paths indicated at 1301, 1302, 1303. The drive assembly interface elements 1304, 1305, 1306 are arranged for engaging with instrument interface elements, for example via drive transfer elements. Movement, such as driven movement, of the drive assembly interface elements 1304, 1305, 1306 along the respective paths 1301, 1302, 1303 causes movement of the drive transfer elements, which causes movement of the instrument interface elements, thereby transferring drive to the instrument.

In an alternative configuration, illustrated in FIG. 13*b*, the drive assembly interface elements can be arranged in a partially staggered configuration. Two of the three drive assembly interface elements, for example the two outermost ones, can be aligned, and the other one, for example the middle one, can be offset from the other two. In an alternative configuration, illustrated in FIG. 13*c*, the drive assembly interface elements can be arranged in a line such that each element is aligned with the others along the direction of movement of each element. Other configurations, including any combination of the configurations described herein, are possible.

In the examples illustrated in FIG. 13, each drive assembly interface element 1304, 1305, 1306 is in the same plane as the other drive assembly interface elements. I.e. they are all movable in the plane of the page of the figure. This need not be the case. Any one or more of the drive assembly interface elements, for example the middle element of three elements, can be movable in a plane offset from the plane or planes in which the other elements are movable.

The different configurations permit flexibility in the arrangement of the interface between the drive assembly interface and the instrument interface. For example, aligning the drive assembly interface elements in a staggered configuration (as in FIG. 13*b*) or in a line (as in FIG. 13*c*) can reduce the width of the interface needed. A reduction in width can also be achieved by offsetting the plane of at least one drive transfer from the plane of at least one other drive transfer element. A configuration can be selected in dependence on a desired width, length and/or depth of the interface.

Suitably the configuration of the motion feedthroughs described herein can accommodate the transfer of drive between drive assembly interface elements configured as illustrated in FIG. 13 at least.

Whilst the motion feedthroughs discussed herein have been introduced separately, any combination of types may be used. For example, a motion feedthrough may comprise one drive transfer element according to one type discussed herein, and another drive transfer element according to one other type discussed herein.

The drape discussed herein need not be a surgical drape, but could be used for non-surgical purposes. For example, it could be used in robotic systems, or systems more generally, in which it is desirable to provide a barrier which permits motion feedthrough. Such a barrier might be a barrier to fluid flow and/or a barrier to particulate matter, for example particulate matter entrained in a flow of fluid such as air. Such a barrier can therefore be used to provide effective protection from chemicals, material filings and/or dust.

The instrument could be used for non-surgical purposes. For example, it could be used in a cosmetic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A motion feedthrough for a surgical drape, the motion feedthrough comprising:
a drive transfer element comprising a first portion and a second portion, the first portion being releasably engageable with a portion of a robot arm and the second portion being releasably engageable with a portion of an instrument, the drive transfer element being linearly movable relative to a bulk portion of the drape so as to transfer drive between the robot arm and the instrument, wherein the motion feedthrough comprises a first longitudinally extending element and a second longitudinally extending element, the first and second longitudinally extending elements being slidingly engageable with one another along at least a portion of their length.

2. A motion feedthrough as claimed in claim 1, in which the motion feedthrough is operable to transfer drive without compromising the integrity of the surgical drape.

3. A motion feedthrough as claimed in claim 1, in which the motion feedthrough is configured to substantially close a hole in the drape and/or be attachable to the periphery of a hole in the drape so as to maintain a substantially hermetic sterile barrier.

4. A motion feedthrough as claimed in claim 1, in which the first longitudinally extending element comprises a tongue and the second longitudinally extending element comprises a groove, the tongue being engagingly receivable within the groove.

5. A motion feedthrough as claimed in claim 1, in which at least one of the first and the second longitudinally extending elements comprises a recess for receiving a plug.

6. A motion feedthrough as claimed in claim 1, in which at least one of the first longitudinally extending element and the second longitudinally extending element is attachable to the periphery of a hole in the drape, so that at least a portion of the drape will move together with the respective longitudinally extending element.

7. A motion feedthrough as claimed in claim 1, in which the motion feedthrough comprises a plurality of drive transfer elements, the drive transfer elements being linearly movable.

8. A motion feedthrough as claimed in claim 1, in which the plurality of drive transfer elements are movable parallel to one another.

9. A motion feedthrough as claimed in claim 1, in which paths defined by movement of each drive transfer element are non-overlapping in a direction transverse to a direction of movement of at least one drive transfer element.

10. A motion feedthrough as claimed in claim 1, in which paths defined by movement of each drive transfer element at least partially overlap in a direction transverse to a direction of movement of at least one drive transfer element.

11. A motion feedthrough as claimed in claim 1, in which paths defined by movement of each drive transfer element are aligned along a common line.

12. A motion feedthrough as claimed in claim 1, in which the motion feedthrough extends generally in a plane, and the drive transfer element is linearly movable in the plane.

* * * * *